US012807912B2

(12) United States Patent
Simon et al.

(10) Patent No.: US 12,807,912 B2
(45) Date of Patent: Nov. 24, 2026

(54) MATERIAL LAYERING DEVICE

(71) Applicant: Axogen Corporation, Alachua, FL (US)

(72) Inventors: Alec Simon, Alachua, FL (US); Kiri Hamaker, Alachua, FL (US); Arunas Zhukauskas, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 545 days.

(21) Appl. No.: 18/374,829

(22) Filed: Sep. 29, 2023

(65) Prior Publication Data

US 2025/0109366 A1 Apr. 3, 2025

(51) Int. Cl.

*C12M 3/00* (2006.01)
*A61L 27/60* (2006.01)
*C12M 1/12* (2006.01)

(52) U.S. Cl.

CPC ............ *C12M 21/08* (2013.01); *C12M 25/06* (2013.01); *C12M 25/14* (2013.01); *A61L 27/60* (2013.01)

(58) Field of Classification Search

CPC ...... C12M 21/08; C12M 25/06; C12M 25/14; A61L 27/60
USPC ........................................................ 435/284.1
See application file for complete search history.

(56) References Cited

U.S. PATENT DOCUMENTS 10,994,913 B2 * 5/2021 Duan-Arnold ......... B65D 65/02
2004/0141887 A1 * 7/2004 Mainquist ........... B01L 3/50855 422/400

* cited by examiner

*Primary Examiner* — Michael L Hobbs
*Assistant Examiner* — Lenora A Abel
(74) *Attorney, Agent, or Firm* — Bookoff McAndrews, PLLC

(57) ABSTRACT

The invention generally relates to devices for manufacture of tissue products, and, more particularly, to material layering assemblies for processing tissue layers to produce a multi-layered tissue product. The invention provides a material layering system to support and/or hold various layers of material to form a multi-layered product.

28 Claims, 14 Drawing Sheets

1300

MATERIAL LAYERING DEVICE

FIELD OF THE INVENTION

The invention generally relates to devices for manufacture of tissue products, and, more particularly, to material layering assemblies for processing tissue layers to produce a multi-layered tissue product.

BACKGROUND

Following one or more of tissue injury, tissue repair, and/or tissue reconstruction, protecting a damaged tissue area may facilitate the healing process. In the case of nerve tissue, failure to cover and/or isolate a nerve repair or nerve injury site may lead to undesired axonal growth into surrounding areas, which may result in soft tissue attachment and scarring. By protecting a nerve repair or injury site (e.g., through covering and isolation), undesired axonal growth may be inhibited (e.g., reduced or eliminated), and, in some instances, healing time may be decreased by directing axonal growth towards a preferred nerve regeneration site, instead of non-targeted areas. Further, such techniques can also help to provide reinforcement to a nerve repair or injury site and help to inhibit separation of coapted nerves.

In order to provide protection and covering at a nerve repair or injury site, membranous tissue grafts in the form of tubes, conduits, sheets for wrapping (i.e., wraps), or other forms for supporting and reinforcing microsurgical repairs of injured nerves may be used. A multi-layer amnion product may be used to help repair tissue, for example, to help repair nerves. However, challenges exist in the manufacture of multi-layered tissue products designed to dry as a sheet product. Accordingly, there is a need for improved devices and methods for preparing multi-layered tissue products.

SUMMARY

The present invention provides a material layering system. In particular, the present invention addresses the challenges of manufacturing a multi-layered tissue product and recognizes that layering tissues, such as placental membranes, together is extremely difficult. The layering process takes place when membranes are wet, which may, for example, cause tissues to retract in response to stretching, to slide when placed on top of one another, and/or to form air bubbles between layers, among other layering difficulties. In order to provide the desired quality for the implant, and for the implant and its manufacture to be commercially viable, each multi-layered tissue product must be scrupulously evaluated for a number of characteristics including delamination, transparency, conformability, repositionability, durability, and suturability. Thus, the invention provides for an improved manufacturing process for achieving a high-quality product while lessening the waste of tissue resources.

The invention provides a material layering system to support and/or hold various layers of material, for example tissue, to form a multi-layered product. In preferred embodiments, the layering systems provide an assembly for forming a multi-layered amnion product, such that the quality of the manufactured tissue product is improved and tissue waste is reduced. Accordingly, the invention provides layering devices/assemblies for improving the manufacture of multi-layered tissue products that allow the tissue layers to maintain a stretched and/or flat orientation without retracting. This allows for more robust layering such that the final dehydrated product may include numerous layers, and can be produced at various thicknesses, retains its shape better, and all of the foregoing, more successfully, than can be achieved without the devices of the invention.

Further, the layering systems of the invention lock each layer into place and thus prevent the tissue layers from sliding and/or bunching. The layering system flattens and compresses the layers together to remove air bubbles and prevent air bubble formation. Accordingly, the layering systems of the invention provide for the manufacture of a highly consistent quality, more consistent product, both in thickness throughout the construct and in the quality of the final product. For example, the devices of the invention provide for a highly durable final product that retains its shape, and does not crumple or bunch. Devices of the invention provide for maximizing the usable amount of each tissue layer such that less tissue is wasted in manufacture. Further, the devices of the invention are easy-to-use, and provide for easy clean-up and sterilizing.

As generally described, the layering systems of the invention may include a layering tool with a first or bottom plate, and may be used in conjunction with a second or top plate. The bottom plate and the top plate may be identical and interchangeable. The bottom plate and the top plate may not be identical but may be interchangeable. The bottom plate and the top plate may not be identical or interchangeable. In non-limiting examples, four or more layers of tissue, such as amnion and/or chorion may be sequentially positioned between the bottom and top plates of the layering tool. For example, the layers of tissue may be sequentially overlaid one on top of the other on the base plate. The base plate may hold the overlaid layers in place relative to each other when stacking the layers. The top plate may then be positioned on top of the overlaid layers to further help hold the layers in place relative to each other once stacked.

Positioning the layers on the layering assembly provides tension to straighten out the layers, to smooth the layers, including to remove air pockets or bubbles between the layers, to size the layers, to organize the layers, and/or to promote uniformity (e.g., facilitate the ability to position the layers so that they overlap with one another to promote consistent or relatively uniform thickness of the resulting multi-layered product. For example, as described in more detail herein, the base plate comprises a face such that, when the materials are layered on the base plate, each layer completely covers the face. Thus, the layers overlap in area of the face to provide a final product that is of a relatively uniform thickness.

In non-limiting examples, the outer edges of the dehydrated multi-layered product may include a sacrificial region aligning with the perimeter region that is trimmed away to produce the final multi-layered product. In some embodiments, the stacked layers substantially or wholly overlap in the sacrificial region. Because of difference in the layers at their respective edges, the layers may not wholly overlap in the sacrificial region. When the sacrificial region is trimmed away, the layers overlap in the area of the face to promote consistent thickness and provide a final product with a relatively uniform thickness. Thus, the stacked layers overlap in the area that remains after trimming the sacrificial area such that a final product with a consistent thickness is achieved.

The layering assemblies generally include in, e.g., a bottom plate and a top plate, a plurality of holes or openings that work in cooperation with specially designed pins to secure each layer to the layering assembly/device. As discussed in more detail herein, the pins may be removably received in the holes of the top and bottom plate for easy clean-up and sterilization. The pins may be integrally formed with the top and/or bottom plate. The pins are designed to pierce tissue layers without piercing a surgical glove to ensure technician safety when working with the tissue product.

Aspects of the invention include a material layering assembly. The material layering assembly includes a base plate comprising a face and a perimeter surrounding the face and comprising a plurality of elongate pins provided along, and extending vertically from a surface of the perimeter of the base plate. The layering assembly includes a top plate comprising a face and a perimeter surrounding the face and comprising a plurality of apertures provided along a surface of the perimeter of the top plate, such that, upon placement of the top plate over the base plate, each of the plurality of apertures provided along the perimeter of the top place is sized and/or shaped to receive a separate respective one of the plurality of elongate pins extending vertically from the surface of the perimeter of the base plate. This aligns the faces of the base and top plates relative to one another and causes one or more layers of material placed upon the base plate, e.g. secured on the plurality of elongate pins of the base plate, to be held between the faces of the base and top plates.

In some embodiments the faces of the base and top plates are elevated relative to the respective perimeters of the base and top plates. In other embodiments, the perimeter of each of the base and top plates comprises a reduced-thickness edge such that the face is raised in relation to the perimeter. Further, in some embodiments, the top plate is aligned over the base plate, the faces of the base and top plates are aligned with one another such that one or more layers of tissue therebetween are compressed between the faces of the base and top plates and the plurality of elongate pins extending from the perimeter of the base plate and received within corresponding apertures of the perimeter of the top plate are not load-bearing.

In some embodiments, each of the base and top plates is of unitary construction. For example, each of the base and top plates is formed from a single piece of material via an additive manufacturing process or a subtractive manufacturing process, in some embodiments.

In some embodiments, each of the plurality of elongate pins is removably attachable to the perimeter of the base plate. For example, in some embodiments, each of the plurality of elongate pins comprises a base section. Further, in particular embodiments, the base section of each of the plurality of elongate pins is configured to releasably fit within a respective aperture provided along the perimeter of the base plate. The base section of each of the plurality of elongate pins is configured to releasably fit within a respective aperture via a slip fit connection, in some embodiments. Further, each of the plurality of apertures provided along the perimeter of the base plate comprises at least a first section having a diameter and length and an opening flush with a surface of the perimeter, in some embodiments. In some embodiments, a length and a diameter of the base section of each of the plurality of elongate pins is less than the length and diameter of the first section of each of the plurality of apertures to thereby create a slip fit tolerance therebetween.

In some embodiments, each of the plurality of elongate pins comprises a top section configured to be received within a separate respective aperture provided along the perimeter of the top plate. In some embodiments, the top section is tapered and comprises a tip for piercing one or more layers of material. In particular embodiments, the top section is cylindrically tapered. The pin tip diameter may be a diameter suitable for piercing the material to be layered. In non-limiting examples, the pin tip diameter may be 0.1 mm, 0.2 mm, 0.3 mm, 0.4 mm, 0.5 mm, 0.6 mm, 0.7 mm, 0.8 mm, 0.9 mm, 1.0 mm or 2.0 mm. For example, in some embodiments, the top section reduces in diameter over 7.50 mm from 2.50 mm to 0.80 mm inclusive at the tip. In some embodiments, the top section reduces in diameter over 7.50 mm from 3.00 mm to 0.80 mm at the tip. In some embodiments, the top section reduces in diameter over 8.00 mm from 3.00 mm to 1.00 mm at the tip.

In some embodiments, the plurality of elongate pins comprises a mid-section configured to be received within a separate respective aperture provided along the perimeter of the top plate. In particular embodiments, each of the plurality of apertures provided along the perimeter of the top plate comprises at least a first section having a diameter and length. For example, in some embodiments, a length and a diameter of the mid-section of each of the plurality of elongate pins is less than the length and diameter of the first section of each of the plurality of apertures provided along the perimeter of the top plate to thereby create a slip fit tolerance therebetween.

In some embodiments, the plurality of elongate pins are placed equidistantly apart along the perimeter of the base plate and the plurality of apertures are correspondingly provided equidistantly apart along the perimeter of the top plate.

In some embodiments, the base plate, the top plate, and the plurality of elongated pins comprise a material that is capable of cleaning, autoclaving, and reuse without warping. For example, in preferred embodiments, the material is stainless steel. In some embodiments, the top plate and/or the base plate are made of a material that that provides a view and/or transparency through the plates, such as a glass or plastic. For example, in some embodiments, the top plate and/or base plate may be constructed from Radel® polyphenylsulfone (PPSU), an amorphous transparent high performance thermoplastic. Such a material is known for its high heat resistance, as well as chemical and impact resistance. Constructing the plates out of a transparent material, such as Radel® PPSU, may allow for a technician view materials provided between the plates and thereby visually inspect and confirm the positioning and/or state of one or more layers of tissue provided between the plates.

In some embodiments, the material used for layering within the material layering assembly is at least tissue. For example, the tissue is placental membrane such that the assembly is configured to hold multiple layers of placental membrane in a fixed position during a vacuum drying process. In specific embodiments, the multiple layers comprise one or more layers of tissue, such as but not limited to an amnion sheet and/or a chorion sheet. Further, in some embodiments, the plurality of elongate pins are configured to pierce the one or more multiple layers of tissue such that each layer is stretched and held in place between the base and top plates and maintained in a substantially flat orientation and prevented from sliding and/or bunching between the faces of the base and top plates. In some embodiments, alignment and placement of the top plate upon the base plate causes the faces of the base and top plates to compress the multiple layers of tissue together and remove and/or prevent air bubble formation and to form a multi-layered construct with a consistent thickness. In other words, adding the top plate over the layers secured on the bottom plate compresses the layers such that air bubbles are removed or prevented, either by virtue of the compression of the layers between the top plate and the bottom plate, or by securing the layers between the top and bottom plates during processing.

DETAILED DESCRIPTION

Figure 1:
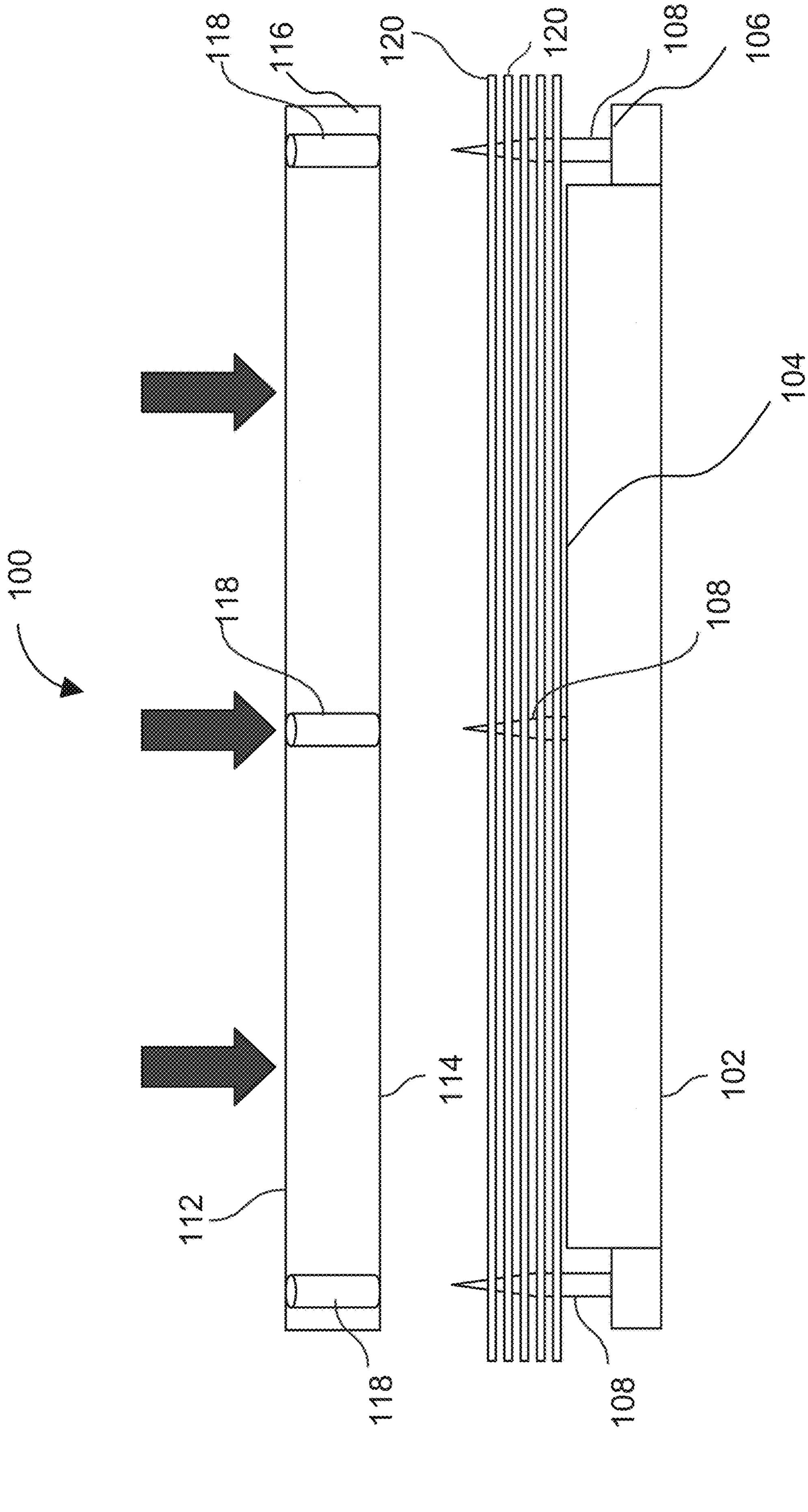
FIG. 1 illustrates a cross sectional view of a material layering assembly in a partially open position according to one embodiment of the disclosure.

The present invention recognizes the challenges associated with manufacturing a multi-layered product and provides a material layering system/assembly designed to support, secure, and compress layers of material such that an improved product is achieved.

The material layering assemblies of the invention may be used in connection with layering any type of material, including any material that might be particularly difficult to handle due to certain characteristics of that material, including, but not limited to, the material being delicate, thin, slippery, shrinks or folds upon itself, and/or is self-sticking if not properly secured.

For example, in some embodiments, the material layering assemblies of the invention may be used for layering certain inanimate materials, such as fabric, a polymer, paper, or the like. In some embodiments, the material layering assemblies may be used for layering tissue, including plant or animal tissue, which may be human or non-human tissue, including, but not limited to, connective tissue, muscle tissue, nervous tissue, and epithelial tissue. It should further be noted that the material layering assembly of the present invention is designed to layer different or similar types of tissues as a layered product.

In preferred embodiments, the layering assembly of the present invention is used for layering biomaterials, which may include natural or synthetic materials particularly useful in medical applications to support, enhance, and/or replace damaged tissue and/or a biological function. For example, in some embodiments, the tissue to be layered via the layering assembly of the present invention may include one or more layers of whole human placental tissue, including, but not limited to, amnion and chorion membranes. It should be noted that, while the following provides a description of the layering assembly of the present invention and the layering of tissue, specifically amnion and/or chorion membrane tissue, the layering assembly may be used for layering any contemplated material, as previously noted herein.

For layering placental membranes, such as amnion or chorion membranes, the layering process takes place when membranes, i.e. tissues, are wet, i.e. prior to being dehydrated, which may, for example, cause tissues to retract in response to stretching, to slide when placed on top of one another, and/or to form air bubbles between layers, among other layering difficulties. In order to provide the desired quality for the implant, and for the implant and its manufacture to be commercially viable, each multi-layered tissue product must be scrupulously evaluated for a number of characteristics including delamination, transparency, conformability, repositionability, durability, and suturability. Thus, the invention provides material layering systems and devices for an improved manufacturing process for achieving a high-quality product while lessening the waste of tissue resources.

As an overview, the material layering assemblies of the invention may be used to stack multiple layers of tissue, and to secure the tissue layers during a vacuum drying process. The material layering assembly allows for tissue layers to maintain a stretched, flat orientation, and locks each layer into place on, for example, a base plate, to prevent sliding and/or bunching while additional layers are added. Further, the material layering assembly provides a top plate to secure the stacked material layers and compress the layers to remove air bubbles and prevent air bubble formation thus providing for the manufacture of a highly consistent product quality with a relatively uniform product thickness throughout the multilayer construct.

Thus, as described in detail herein, the material layering assembly of the present invention may be used to support and/or hold various layers of tissue to form, for example, a multi-layer amnion (MLA) or amnion/chorion product. For example, a plurality of layers of amnion and/or amnion/chorion may be sequentially positioned on a base plate of the material layering assembly, one on top of the other, such that the device provides for one or more of: holding the layers in place relative to each other when stacking them; providing tension to straighten out the layers, smooth the layers, and size the layers; organizing the layers; promoting uniformity (e.g., facilitate the ability to position the layers so that they substantially overlap with one another in the same areas to promote consistent thickness of the resulting MLA product); and improving the amount of product manufactured (e.g. product yield) while reducing tissue waste.

Positioning the layers on the layering assembly provides tension to straighten out the layers, to smooth the layers, including to remove air pockets or bubbles between the layers, to size the layers, to organize the layers, and/or to promote uniformity (e.g., facilitate the ability to position the layers so that they overlap with one another to promote consistent or relatively uniform thickness of the resulting multi-layered product. For example, as described in more detail herein, the base plate comprises a face such that, when the materials are layered on the base plate, each layer completely covers the face. Thus, the layers overlap in area of the face to provide a final product that is of a relatively uniform thickness.

In non-limiting examples, the outer edges of the dehydrated multi-layered product may include a sacrificial region aligning with the perimeter region that is trimmed away to produce the final multi-layered product. In some embodiments, the stacked layers substantially or wholly overlap in the sacrificial region. Because of difference in the layers at their respective edges, the layers may not wholly overlap in the sacrificial region. When the sacrificial region is trimmed away, the layers overlap in the area of the face to promote consistent thickness and provide a final product with a relatively uniform thickness. Thus, the stacked layers overlap in the area that remains after trimming the sacrificial area such that a final product with a consistent thickness is achieved. FIG. 1 illustrates a side view of a material layering assembly 100 in a partially closed position according to one embodiment of the disclosure. The material layering tool includes at least a first base or bottom plate and a second top plate designed to work in conjunction with each other to secure, support, hold, and, in some embodiments, compress layers of material placed within the material layering assembly. As illustrated in FIG. 1, the top plate may close or be urged upon the layers secured on the base plate to compress the layers of material placed within the device.

In one aspect, the invention discloses a material layering assembly 100 that includes a base plate 102 comprising a face 104 and a perimeter 106 surrounding the face 104 and comprising a plurality of elongate pins 108 provided along, and extending vertically from, the perimeter 106 of the base plate 102. Further, the material layering assembly 100 includes a top plate 112 comprising a face 114 and a perimeter 116 surrounding the face 114 and comprising a plurality of apertures 118 provided along a surface of the perimeter 116 of the top plate such that, upon placement of the top plate 112 over the base plate 102, each of the plurality of apertures 118 provided along the perimeter 116 of the top place 112 is sized and/or shaped to receive a separate respective one of the plurality of elongate pins 108 extending vertically from the perimeter 106 of the base plate 102. Thus, the face 104 of the base plate 102 and the face 114 of the top plate 112 align relative to one another and cause one or more layers of material 120 placed upon the base plate 102 to be held between the faces of the base 102 and top 112 plates.

In some embodiments, the face 104 of the base plate 102 may be an elevated platform relative to the perimeter 106 of the base plate 102. Likewise, the face 114 of the top plate 112 may be an elevated platform relative to the perimeter 116 of the top plate.

Figure 2:
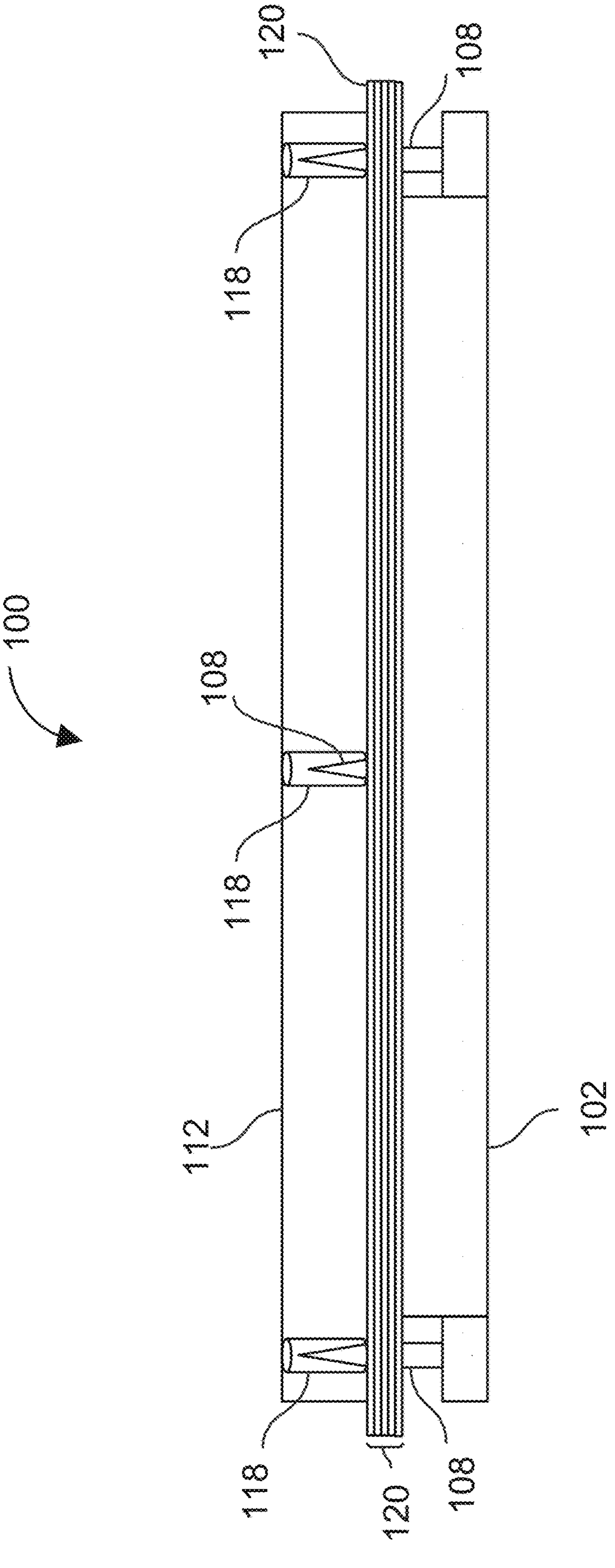
FIG. 2 illustrates a side view of a material layering assembly in a closed configuration according to one embodiment of the disclosure.

FIG. 2 illustrates a cross-sectional view of a material layering assembly 100 in a closed position according to one embodiment of the disclosure. As shown, multiple layers of tissue 120 are compressed and secured between the top plate 112 and the bottom plate 102 of the layering assembly 100. Each of the pins 108 may be aligned in a respective aperture 118 or hole of the top plate 112. As is discussed in more detail herein, in some embodiments, the base plate 102 and the top plate 112 may be identical and interchangeable. In some embodiments, the base plate and the top plate may not be identical but may be interchangeable. In some embodiments, the base plate and the top plate may not be identical or interchangeable. As discussed in more detail herein, the material layering assembly 100 may be used to help support and/or hold various layers of tissue, for example, to form a multi-layered amnion (MLA) product.

The material layering assembly 100 may be any suitable shape, e.g., generally rectangular or square, and any suitable size. The size of material layering assembly 100 may be greater than or approximately equal to the size of the intended resulting multi-layered tissue product.

In non-limiting examples, the base plate and the top plate may have a length or width of approximately 5 cm to approximately 20 cm, approximately 5 cm to approximately 15 cm, approximately 5 cm to approximately 10 cm, approximately 8 cm×approximately 8 cm, approximately 10 cm×approximately 10 cm, approximately 12 cm×approximately 12 cm, etc. In some embodiments, the material layering assembly 100 size, and associated base and top plates, may be designed based on the size of the tissue layers with which it will be used.

Figure 3:
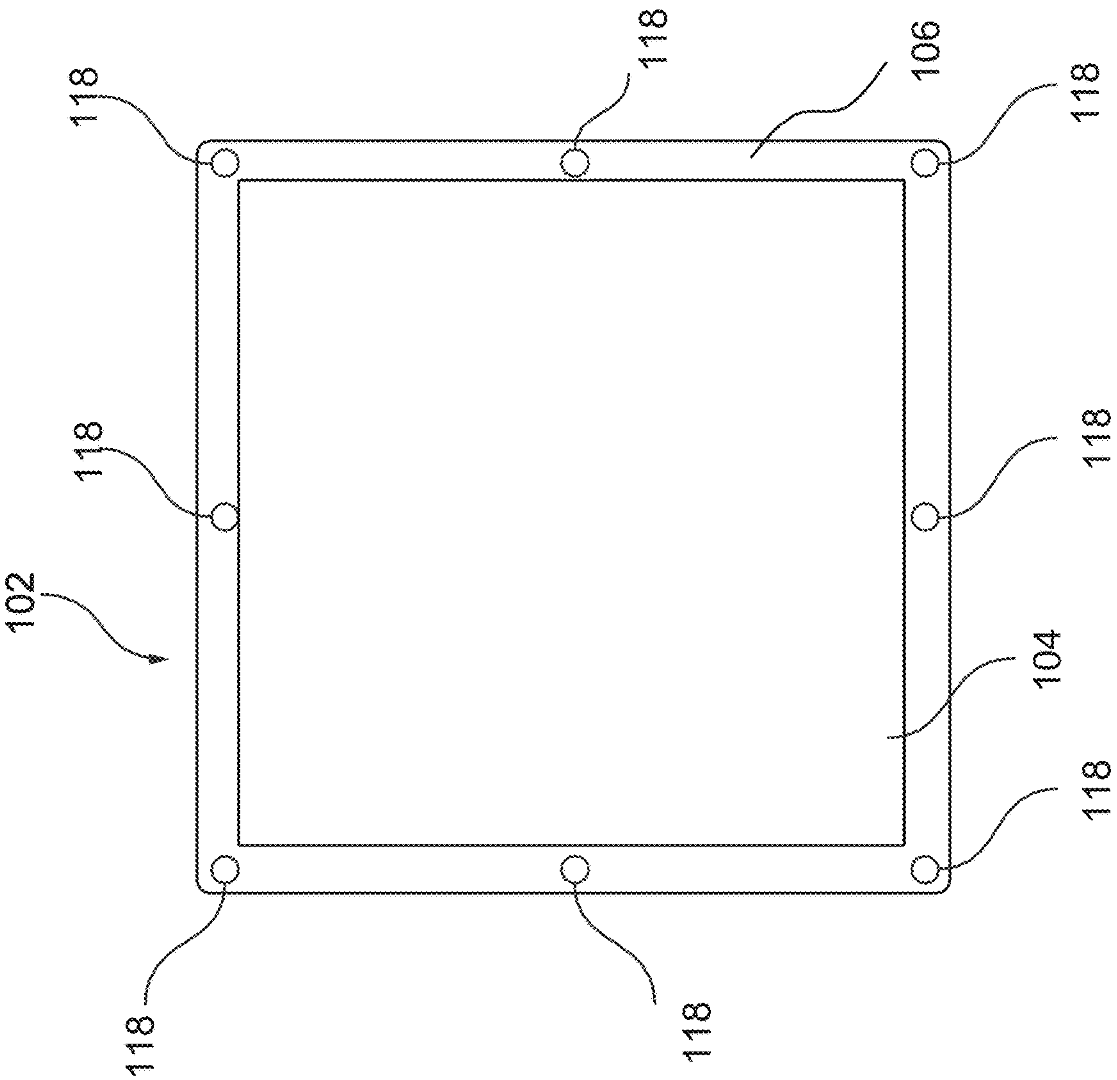
FIG. 3 is a plan view of a first or base plate according to one embodiment of the invention.

FIG. 3 illustrates a plan view of a first or base plate 102 of a material layering assembly 100 according to one embodiment of the invention. As used herein, the material layering assembly may be alternatively referred to as a layering tool or device. As previously noted, in some embodiments, the base plate and the top plate may be of the same design and therefore identical and/or interchangeable. The base plate 102 may include a plurality of apertures 118 or holes within which to fit the elongate pins 108. Thus, the pins 108 may be removably fit within the apertures 118 or holes in the base plate 102, or, in embodiments wherein the base plate and the top plate are identical and interchangeable, the pins 108 may removably fit within the apertures of the plate used as the base plate.

The base plate 102 may include an elevated face 104 or elevated face relative to the base. The elevated face 104 or elevated face may have a shape that corresponds to a shape of the base plate and/or top plate of the material layering assembly. In some embodiments, the face of the base plate and/or the top plate are elevated relative to the respective perimeters of the base and top plates. In some embodiments, the perimeter of each of the base and top plates comprises a reduced-thickness edge such that the face is raised in relation to the perimeter.

In some embodiments, when the top plate 112 is aligned over the base plate 102, the faces of the base and top plates are aligned with one another such that one or more layers of tissue therebetween are compressed between the face 104 of the base plate and the face 114 of the top plate, and held via the plurality of elongate pins 108 extending vertically from the perimeter 106 of the base plate and received within corresponding apertures of the perimeter 116 of the top plate. In some embodiments, the plurality of elongate pins 108 extending from the perimeter 106 of the base plate and received within corresponding apertures of the perimeter 116 of the top plate are not load-bearing.

Figure 4:
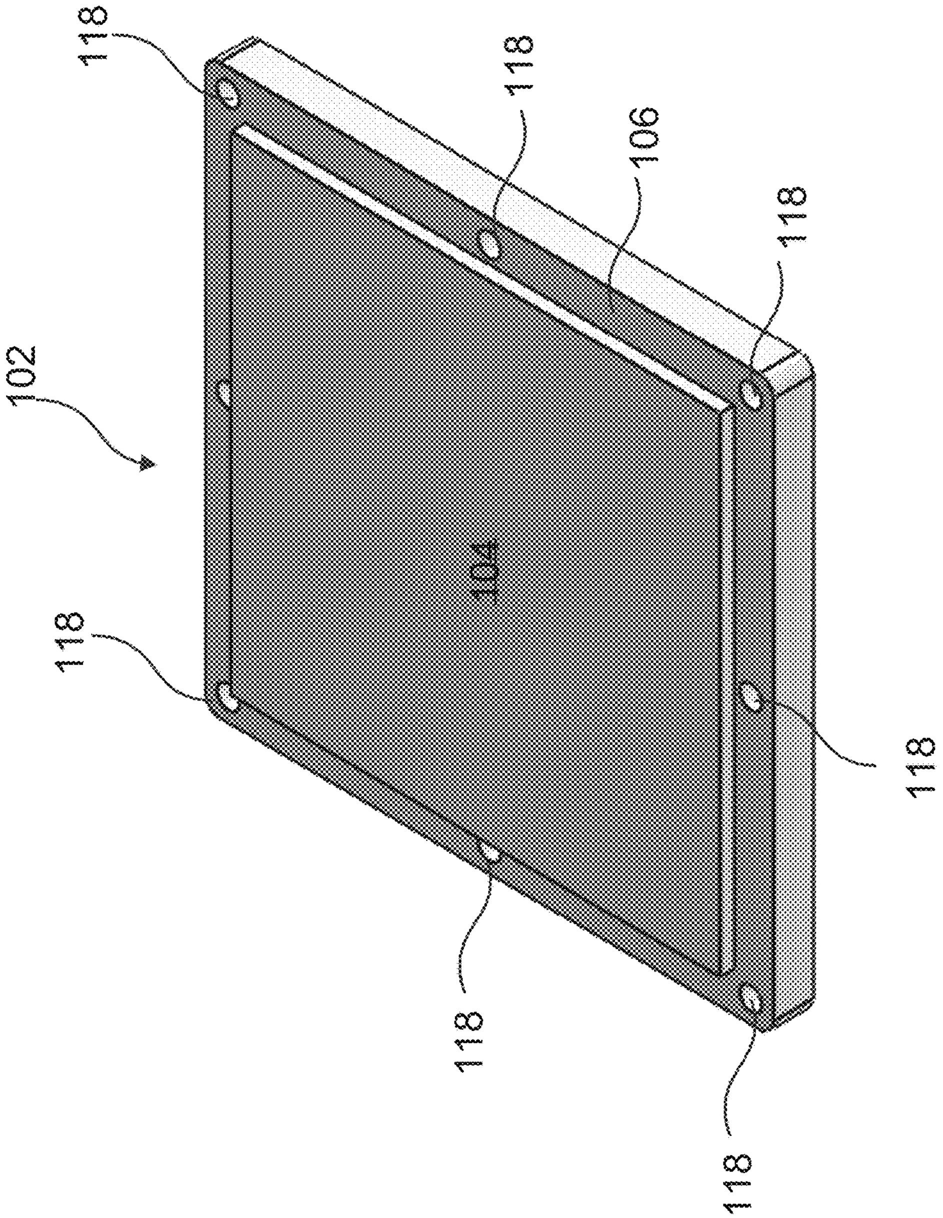
FIG. 4 is a perspective view of a first or base plate according to one embodiment of the material layering assembly of the invention.

FIG. 4 illustrates a perspective view of one embodiment of a base plate 102 of the material layering assembly. As noted, if the base plate 102 and the top plate 112 of the material layering assembly 100 are identical and/or interchangeable, the illustrations of FIGS. 3 and 4 would also apply to the top plate of the material layering assembly.

In non-limiting examples, if the base plate 102 of the material layering assembly 100 is generally rectangular or square, then elevated face or face 104 may also be generally rectangular or square. Elevated face or face 104 may be approximately 70% to approximately 95% of the size (length or width) of material layering assembly 100. If the material layering assembly base and top plates are approximately 12 cm×approximately 12 cm, then the associated elevated face or face may be approximately 9 cm×approximately 9 cm, approximately 11 cm×approximately 11 cm, for example, approximately 10.6 cm×approximately 10.6 cm. If the material layering assembly base and top plates are approximately 10 cm×approximately 10 cm, then the associated elevated face or face may be approximately 8.6 cm×approximately 8.6 cm. Alternatively, if the material layering assembly base and top plates are approximately 8 cm×approximately 8 cm, then the associated elevated face or face may be approximately 6.6 cm×approximately 6.6 cm. In some embodiments, the material assembly base and/or top plates are 6 cm×6 cm. However, it is noted that the material layering assembly base and top plates and the entire material layering assembly itself may be any suitable dimensions for manufacturing a layered material product. Further, although the examples described above are in terms of rectangles, and specifically, squares, any suitable shape may be used. For example, the base and top plates of material layering assembly 100 may be individually rounded (e.g., circular), hexagonal, etc., and may be identical and/or interchangeable or not identical and/or interchangeable depending on the material to be layered between the base plate and the top plate.

In some embodiments, the different sizes of top plates and base plates for the material layering assemblies disclosed herein may have the same size apertures or holes and pins for easily interchanging the respective plates of the material layering assemblies.

As disclosed in more detail herein, in some embodiments, the elevated face 104 may have a thickness of approximately 10% to approximately 40% of a thickness of the material layering assembly plates or as a whole. For example, if a base plate 102 of the material layering assembly 100 has a total thickness of approximately 9.5 mm (i.e., including a thickness of an elevated face 104), then elevated face 104 itself may include a thickness of approximately 2.5 mm.

Figure 5:
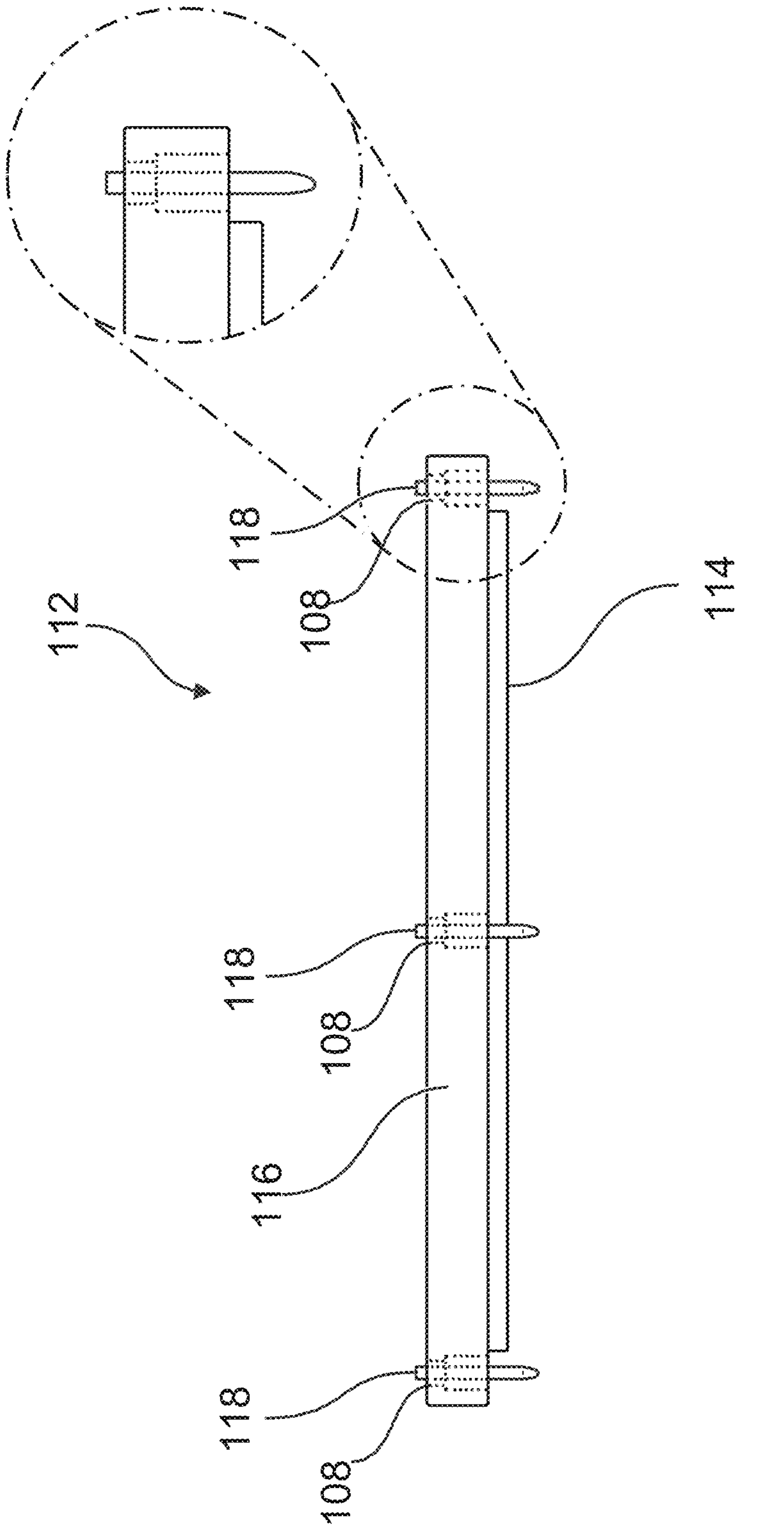
FIG. 5 illustrates a cross-sectional view of a top plate of a material layering assembly according to one embodiment of the disclosure.

FIG. 5 illustrates a cross-sectional view of a top plate 112 of a material layering assembly according to one embodiment of the disclosure. The top plate may include a plurality of apertures 118, openings, or holes. The apertures 118, openings, or holes may be positioned on a perimeter 106 of the bottom plate and/or a perimeter 116 of the top plate. The apertures 118 or holes may extend through an entire width or a portion of a width of the base plate 102 or the top plate 112 of the material layering assembly. The plurality of apertures 118 may extend inward. The apertures or holes may be positioned in one or more of the corners of each of the base plate 102 and/or the top plate 112, for example around the perimeter 106 of the base plate or the perimeter 116 of the top plate outside of the elevated face of each plate. In non-limiting examples, the apertures 118 or holes may be positioned in each corner of the base plate and/or the top plate, and/or equidistant along the perimeter sections of one or both plates. In some embodiments, the apertures 118 or holes are positioned in the side or middle portions of the base plate and/or top plate. In some embodiments, the apertures are randomly spaced in the perimeter section of the base plate and/or the top plate such.

In non-limiting examples, for a base plate and/or a top plate that is rectangular, an aperture or hole or a plurality of holes may be positioned on each of the sides (e.g., the top, bottom, left, and right sides) of one or both of the base and/or top plate of the material layering assembly. Likewise, for base plates and/or top plates that are not rectangular or square in shape, such as for material layering assemblies that are a round shape, hexagonal, and/or triangular, in non-limiting examples, the plurality of apertures or holes may be positioned anywhere on the base and/or top plate that facilitates securing a material to the base and/or top plate. Thus, apertures or holes positioned on the side of the one or both of the base plate and/or top plate may be placed at any position on the bottom and/or top plate to facilitate securing the type of tissue and/or material between the two plates.

In a non-limiting example, apertures or holes positioned on the outer edges or sides of the base plate and/or top plate, e.g. in a perimeter section, may be positioned between (e.g., mid-way between) apertures or holes in respective corners of each plate. In some embodiments, if the base or top plate is approximately 12 cm, then one or more apertures or holes may be positioned approximately 6 cm from the respective corners of each plate.

Apertures or holes may be positioned around the perimeter of each plate and may be positioned around each elevated face, i.e. in the perimeter section of the respective plate. As shown in FIG. 4, an example base plate may include eight apertures 118 or holes, although any suitable number of apertures or holes may be incorporated. In some instances, the number of apertures or holes may depend, at least in part, on the shape of the material layering assembly, the size of the material layering assembly, and/or the type of material to be layered within the material layering assembly.

Apertures 118 or holes may be blind holes extending through only a portion of each plate. For example, if the portion of each of the base and/or top plate extends radially beyond the elevated face includes a thickness of approximately 7.0 mm, then the apertures or holes may extend less than 7.0 mm, e.g., approximately 5.0 mm, through the base and/or top plate. Alternatively, the apertures or holes may be through holes, for example, extending through an entirety (e.g., an entire thickness) of one or both of the base plate and/or the top plate. Alternatively or additionally, as shown in FIG. 5, the apertures or holes may include one or more narrowed or tapered sections, for example, a first wider portion and a second narrower or tapered section. In some embodiments, the plurality of apertures or holes provided along the perimeter of the base plate may include at least a first section having a diameter and length and an opening flush with a surface of the perimeter. In other embodiments, the apertures or holes may include the same or similar circumference (i.e., no narrowed or tapered sections) along the depth of the apertures or holes.

The apertures or holes may be designed to work in cooperation with the one or more elongate pins 118. The pin and aperture/hole combination may be any combination that supports, secures, and aligns the bottom plate with the top plate and the material secured therebetween. The pins and apertures may be designed to meet the requirements necessary for layering a specific material within the material layering assembly. The pins may be positioned in either or both of the top plate and the bottom plate to suit the needs of the layering procedure. The pins may be removably received in the holes of the top and bottom plate for easy clean-up and sterilization. The pins may be integrally formed with the top and/or bottom plate. The pins are designed to pierce tissue layers without piercing a surgical glove to ensure technician safety when working with the tissue product.

Figure 6:
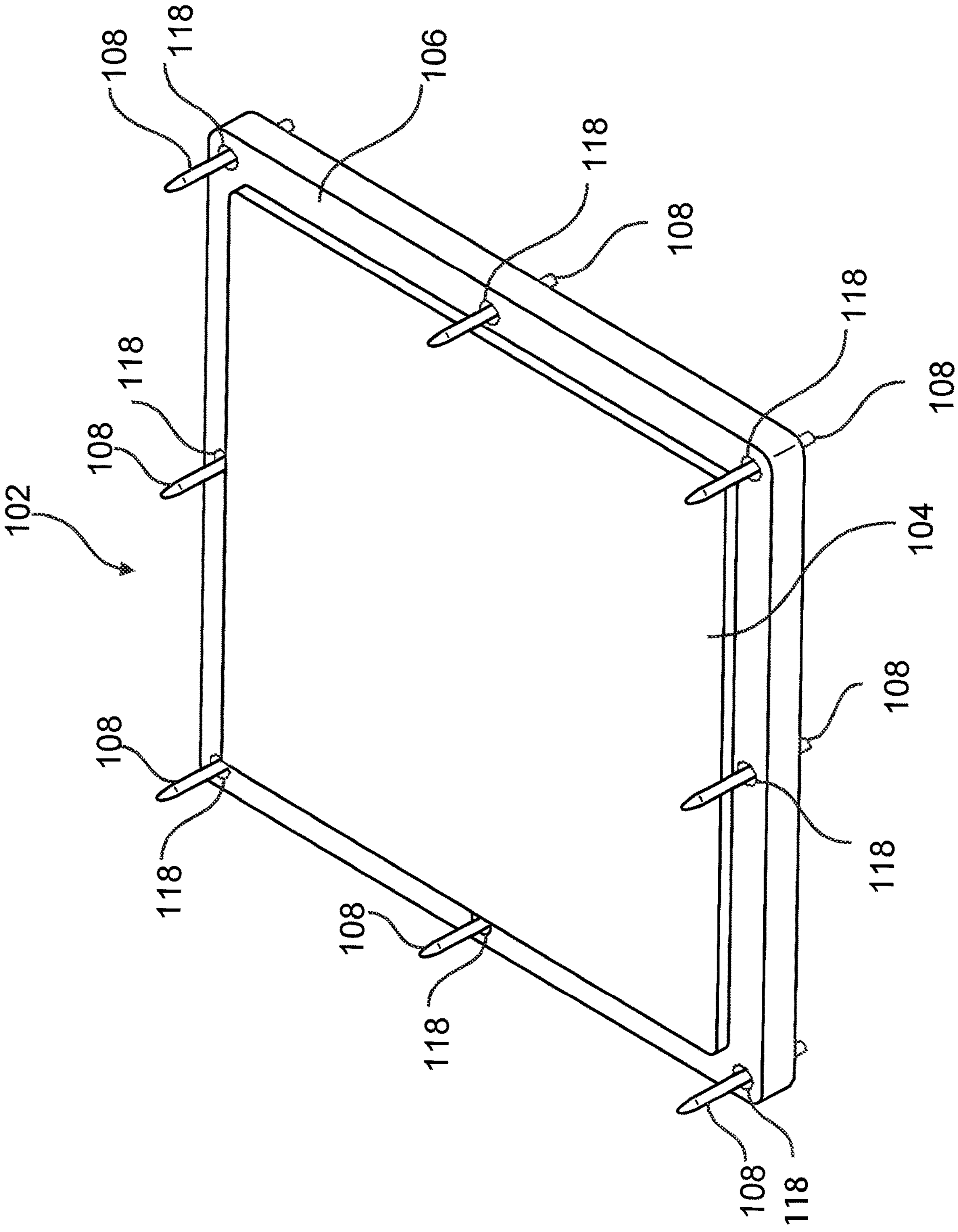
FIG. 6 illustrates a perspective view of a base plate or top plate in which pins are positioned within apertures or holes of the base plate or top plate according to one embodiment of the disclosure.

FIG. 6 illustrates a perspective view of a base plate or top plate in which pins are positioned within apertures or holes of the base plate or top plate according to one embodiment of the disclosure. For example, the apertures or holes may be through holes and the pins may include a head with a larger diameter than the aperture or hole such that the pin head is stopped at the surface of the base or top plate and prevents the pin from going all the way through the aperture or hole. The pin may therefore protrude out of the aperture or hole, for example on the base plate, facing up such that the pin tips may pierce the material layered onto the base plate platform and secure the layers of material to the base or bottom plate. The pins may then be aligned with the apertures or holes of the top plate to position the top plate over the material secured by the pins to the base plate. Alternatively or additionally, the pins may be secured in the top plate and may be aligned over apertures or holes in the base plate in the same way.

In some embodiments, the pin may include a head that is the same diameter of the aperture or hole such that the head of the pin may be tapped into the aperture or hole. In this way, a force may be applied to the head of the pin to not only tap the pin into a respective aperture or hole, but to align the pins with the respective hole and/or pierce the material held within the material layering assembly.

Figure 7:
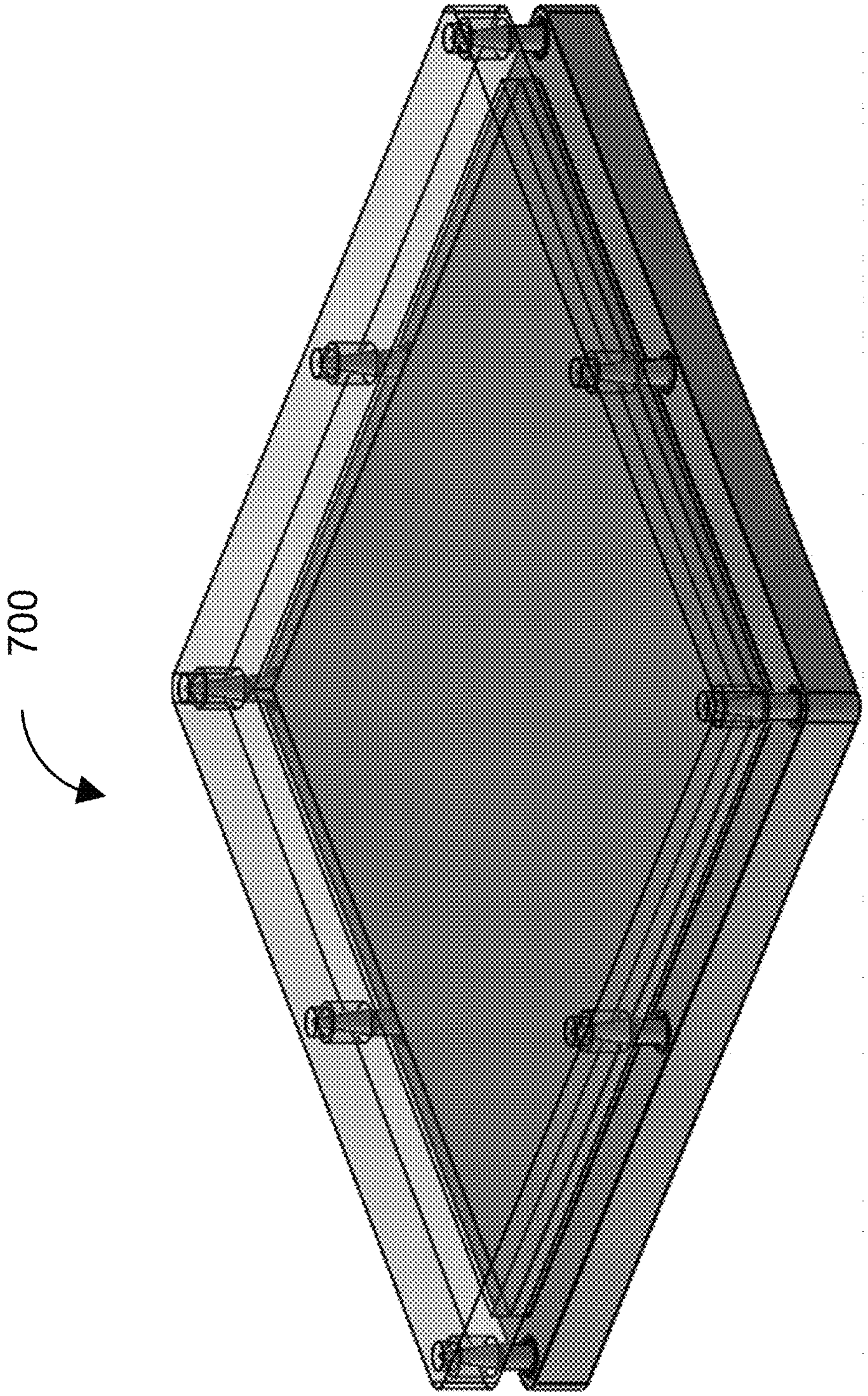
FIG. 7 illustrates a perspective view of one embodiment of a material layering assembly in a closed configuration with a top plate positioned on a base plate, and with the pins and respective apertures aligned.

FIG. 7 illustrates a perspective view of one embodiment of a material layering assembly 700 in a closed position with a top plate positioned on a base plate, and with the pins and respective apertures aligned. For example, in some embodiments, the aperture or hole may be a blind hole with a diameter only slightly larger than the pin such that the pin fits within the aperture or hole via a slip fit. In this way, the pins may be removeable from the apertures or holes. Additionally, in some embodiments in which the top plate and the base plate are identical and/or interchangeable, pins may be placed within the apertures or holes of the base plate such that, when the top plate is placed over the base plate, the apertures or holes of the top plate are aligned with the pins secured within the apertures or holes of the base plate. In some embodiments, the aperture or hole may be a threaded hole and the pin a threaded pin such that the pin may screw into a respective hole. In some embodiments, the base section of each of the plurality of elongate pins is configured to releasably fit within a respective aperture via a magnetic connection. The number of apertures or holes, and corresponding elongate pins are designed such that pins do not lose contact with tissue once the tissue is layered on the base plate to keep the layers firmly secured and prevent loss of the resulting construct if a layer becomes unsecured.

Figure 8:
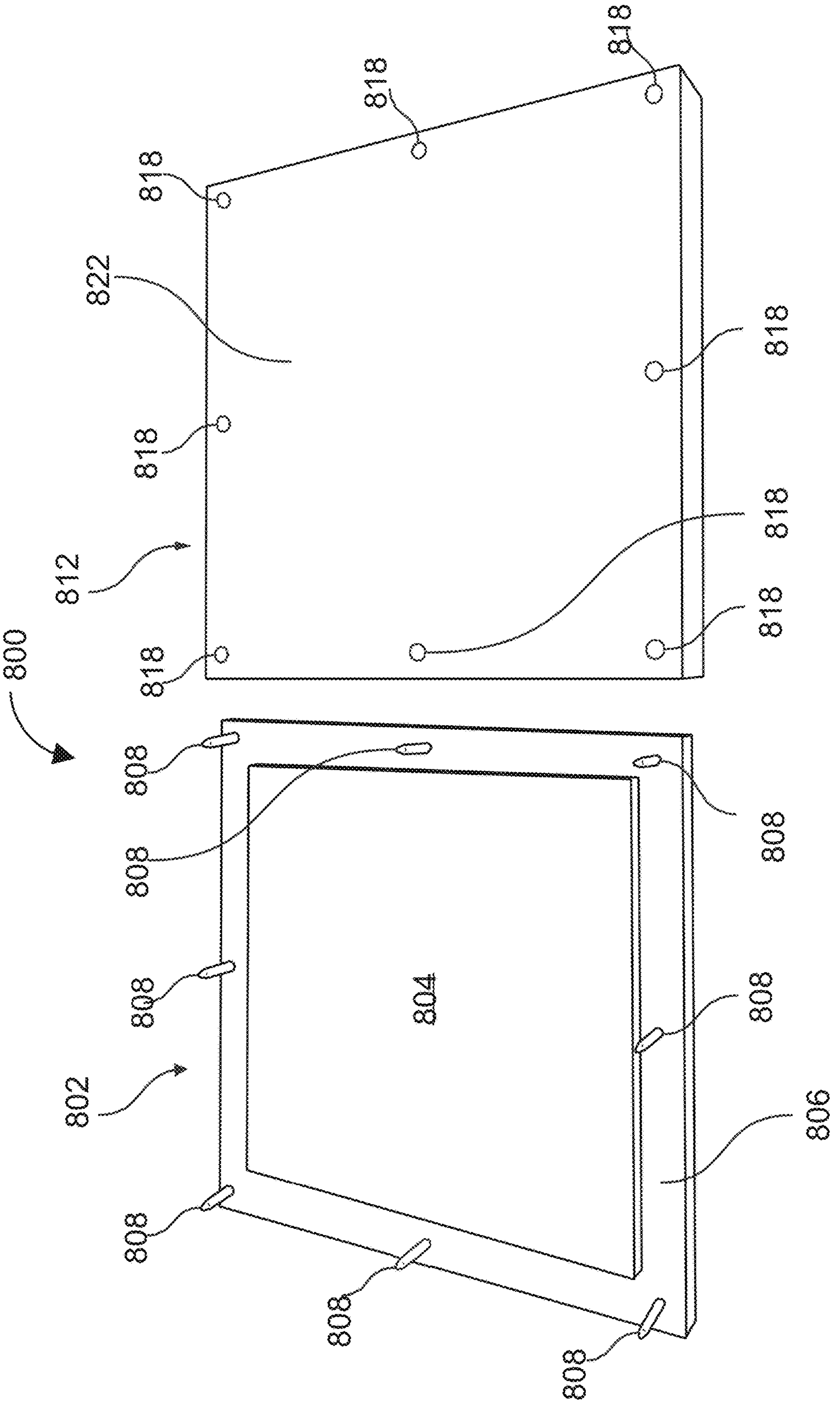
FIG. 8 illustrates a plan view of a material layering assembly in an open configuration according to one embodiment of the invention.

FIG. 8 illustrates a plan view of a material layering assembly 800 according to one embodiment of the invention, in an opened configuration illustrating a base plate 802 and a corresponding top plate 812. As illustrated, the base plate 802 and the top plate 812 are not identical. In some embodiments, the top plate 812 may generally be the same or similar size and/or shape as the bottom or base plate 802.

In some embodiments, the base plate 802 includes an elevated face 804 and a perimeter 806 space surrounding the elevated face, with a plurality of apertures 818 positioned within the perimeter 806 space. As illustrated, the plurality of pins 808 may be positioned within the apertures 818 of the base plate 802 extending vertically from the apertures 818 positioned within the perimeter 806. In some embodiments, the plurality of pins 808 may be part of a unitary construction of the base plate and therefore may not be positioned within apertures of the base plate but rather may be integrally formed as part of the base plate. Thus, the pins 808 may be integrally formed with either of the base plate 802 or the top plate 812, for example, surrounding the elevated face 804 or face 822 in the positions described herein. In other embodiments, the plurality of pins may be removably placed into the apertures of the base plate.

As illustrated, the top plate 812 may include a plurality of apertures 818 or holes corresponding to the pins 808 associated with the bottom plate 802. The top plate may include a face 822 designed to be advanced or otherwise positioned toward the base plate 802 to press and secure the layers of material. The face 822 may be smooth and flat with no elevated face. The face may be designed such that air bubbles are removed or prevented from forming within the layers of material secured within the material layering assembly. In other embodiments, the face may be elevated relative to the perimeter of the top plate. The top plate 812 may include a plurality of apertures 818, openings or holes. The apertures may be blind holes, through holes, tapered holes, consistent diameter holes, etc. The apertures 818 may be positioned in the top plate 812 to at least partially correspond to the positions of pins 808 associated with the base plate 802, for example, when the top plate 812 is positioned above or on the bottom of the base plate 802.

In some embodiments, each of the base and top plates is of unitary construction. For example, in some embodiments, each of the base and top plates is formed from a single piece of material via an additive manufacturing process, for example 3-dimensional (3D) printing, or a subtractive manufacturing process, for example via CNC laser or friction cutting. In some embodiments, the material layering tool is constructed from a mold, for example via injection molding. The material layering tool may be a material of a solid structure capable of supporting and compressing the material layers secured between the base plate and the top plate. In some embodiments, the material layering assembly is capable of being cleaned, autoclaved, and reused without warping. In some embodiments the material layering assembly is of a single use, and/or disposable construction. In some embodiments, the base plate, top plate, and plurality of elongated pins comprise a same or different material that is capable of cleaning, autoclaving, and reuse without warping. For example, in some embodiments, the material is stainless steel.

In some embodiments, the material layering assembly is constructed of a metal, for example, stainless steel. In some embodiments the base plate and the top plate are solid stainless steel. The stainless steel may be one or more grades, for example the base plate and top plate may be 304 stainless steel and the plurality of pins may be 316 stainless steel. In some embodiments, the material layering assembly is constructed of glass. In some embodiments, the material layering tool is constructed of a biocompatible plastic capable of autoclaving, for example, Nalgene, Polypropylene (PP), polypropylene copolymer (PPCO), polyoxymethylene (POM), polyether ketone (PEEK), and/or a fluoropolymer such as Teflon PFA, fluorinated ethylene propylene (FEP), or Ethylene tetrafluoroethylene (ETFE). In some embodiments, the top plate and/or the base plate are made of a material that provides a view and/or transparency through the plates, such as a glass or plastic.

For example, in some embodiments, the top plate and/or base plate may be constructed from Radel® polyphenylsulfone (PPSU), an amorphous transparent high performance thermoplastic. Such a material is known for its high heat resistance, as well as chemical and impact resistance. Constructing the plates out of a transparent material, such as Radel® PPSU, may allow for a technician view materials provided between the plates and thereby visually inspect and confirm the positioning and/or state of one or more layers of tissue provided between the plates.

Figure 9:
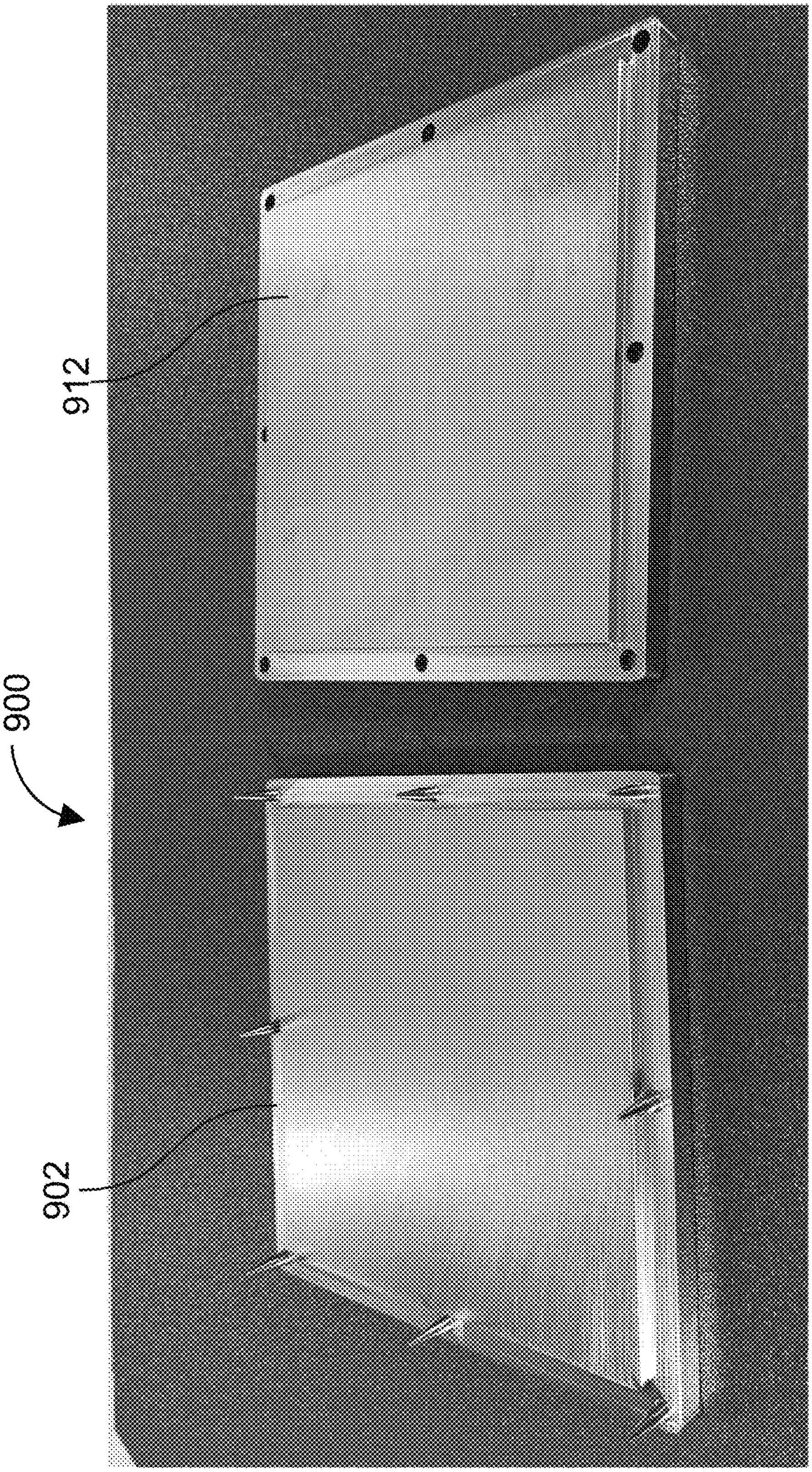
FIG. 9 illustrates a material layering assembly according to one embodiment of the disclosure in which the base plate and the top plate are identical and interchangeable.

FIG. 9 illustrates a material layering assembly 900 according to one embodiment of the disclosure in an open configuration in which the base plate 902 and the top plate 912 are identical and interchangeable. As discussed in more detail herein, and as shown, the pins may all be the same size and may be placed in any of the apertures or holes positioned on the perimeter of each plate, for example the eight apertures or holes as illustrated. Alternatively, the apertures and/or elongate pins may be of different sizes and the apertures or holes may be positioned at any point on either of the base plate and/or top plate to suit the needs of the type of material to be layered between the plates. In some embodiments, the elongate pins may be removably placed within the apertures of either the base plate and/or the top plate. As illustrated, the material layering assembly may be constructed of a metal, for example, stainless steel.

Figure 10A:
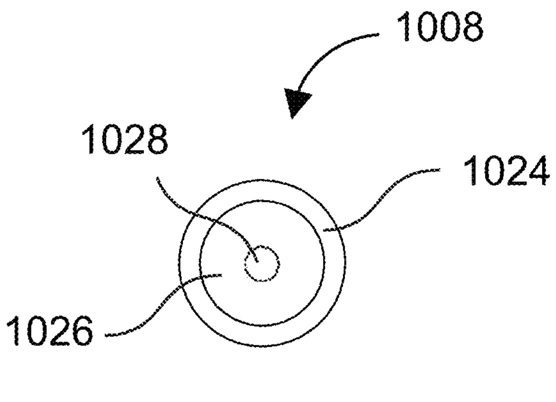
FIGS. 10A, 10B, and 10C illustrate a pin according to one embodiment of a material layering assembly of the disclosure.
Figure 10B:
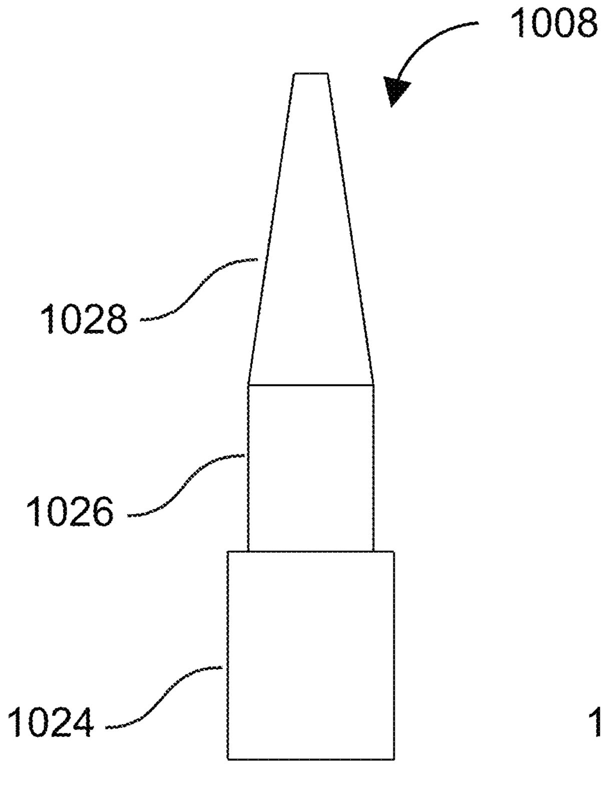
Figure 10C:
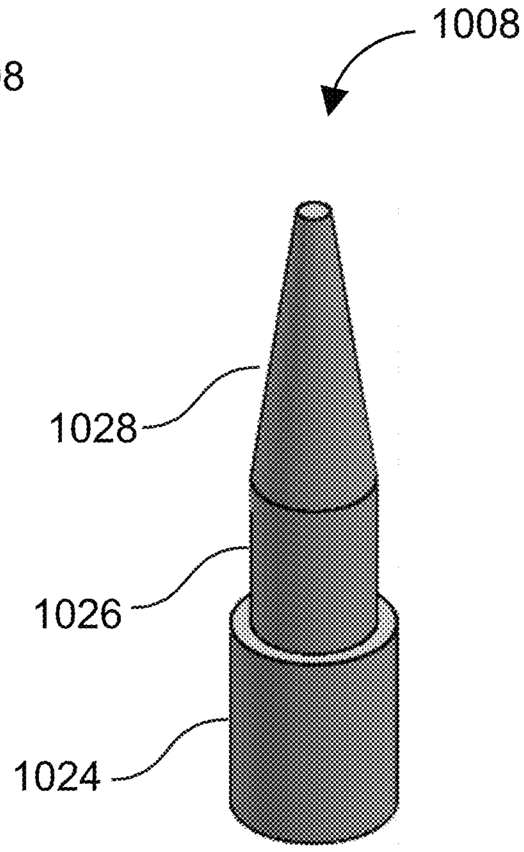

FIGS. 10A, 10B, and 10C illustrate an elongate pin 1008 according to one embodiment of a material layering assembly of the disclosure. FIG. 10A illustrates a top plan view of one of a plurality of elongate pins 1008 designed to releasably fit within a respective aperture or hole of the base plate or the top plate via a slip fit connection, according to one embodiment of the disclosure. The releasable or removable plurality of elongate pins may be stainless steel, for example 316 stainless steel. As described in detail herein, the plurality of pins may be designed such that they are easily removed from the apertures or holes for cleaning and autoclaving. In some embodiments, the elongate pins fit into the holes without impact and are not load bearing.

FIG. 10B illustrates a side plan view of an elongate pin according to one embodiment of the disclosure. FIG. 10C illustrates a perspective view of an elongate pin according to one embodiment of the disclosure. In some embodiments, the plurality of elongate pins are thus removably attachable to the perimeter of, for example, the base plate and/or the top plate. For example, the elongate pin may comprise a base section 1024 such that the base section of each of the plurality of elongate pins is configured to releasably fit within a respective aperture provided along the perimeter of the base plate. The base section 1024 may have a length and diameter that is different than a length and diameter of the rest of the elongate pin. The plurality of pins may further comprise a midsection 1026 with a diameter that is different than the base section 1024 of the elongate pin.

The elongate pins may comprise a top section 1028 with a length and/or diameter different than the length and/or diameter of either of the midsection 1026 and/or the base section 1024. The top section may be configured to taper cylindrically to a tip for piercing one or more layers of material. The pin tip diameter may be a diameter suitable for piercing the material to be layered. In non-limiting examples, the pin tip diameter may be 0.1 mm, 0.2 mm, 0.3 mm, 0.4 mm, 0.5 mm, 0.6 mm, 0.7 mm, 0.8 mm, 0.9 mm, 1.0 mm or 2.0 mm. For example, in some embodiments of the elongate pins, the top section reduces in diameter over 7.50 mm from 2.50 mm to 0.80 mm inclusive at the tip. In some embodiments, the top section reduces in diameter over 7.50 mm from 3.00 mm to 0.80 mm at the tip. In some embodiments, the top section reduces in diameter over 8.00 mm from 3.00 mm to 1.00 mm at the tip. These examples are meant to be non-limiting, and it is noted that the top section of the elongate pins may reduce in diameter to a tip in any range to suit the needs for layering material in the material layering assembly. Thus, the pin tip diameter may be a diameter suitable for piercing the material to be layered. As noted above, in non-limiting examples, the pin tip diameter may be 0.1 mm, 0.2 mm, 0.3 mm, 0.4 mm, 0.5 mm, 0.6 mm, 0.7 mm, 0.8 mm, 0.9 mm, 1.0 mm or 2.0 mm. For example, reduction in diameter of the top section of the elongate pins may be configured to define a point at the tip that is sufficient to pierce tissue without piercing a surgical glove, thus providing a safety feature for technicians layering material such as biological tissue. Further, the tip of the elongate pins may be configured to pierce tissue without tearing tissue and without piercing a common surgical glove. The elongate pins may be of a diameter that does not tear tissue and provides for securing the tissue to the base plate without tearing the tissue.

In some embodiments, the elongate pins have a standard diameter for the base section that fits via a slip fit within a standard sized aperture or hole of the base plate such that the pin midsections and top sections can vary to easily change to different sized or shaped pins, thus accommodating different types of material layering within the material layering assembly. In some embodiments, the pins are inserted into the apertures or holes without force. In some embodiments, the pins are inserted into the apertures or holes with a slight force.

Figure 11A:
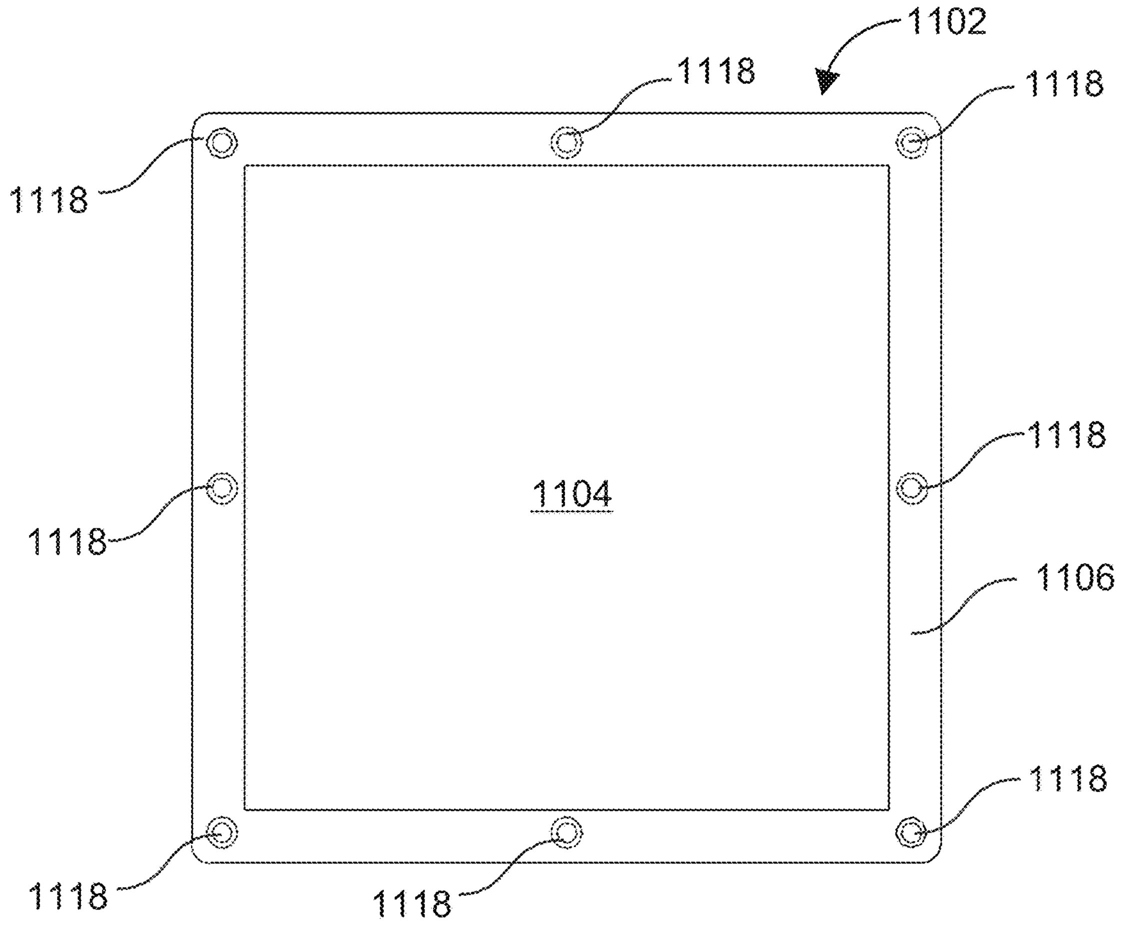
FIGS. 11A and 11B illustrate a base plate according to one embodiment of the disclosure.
Figure 11B:
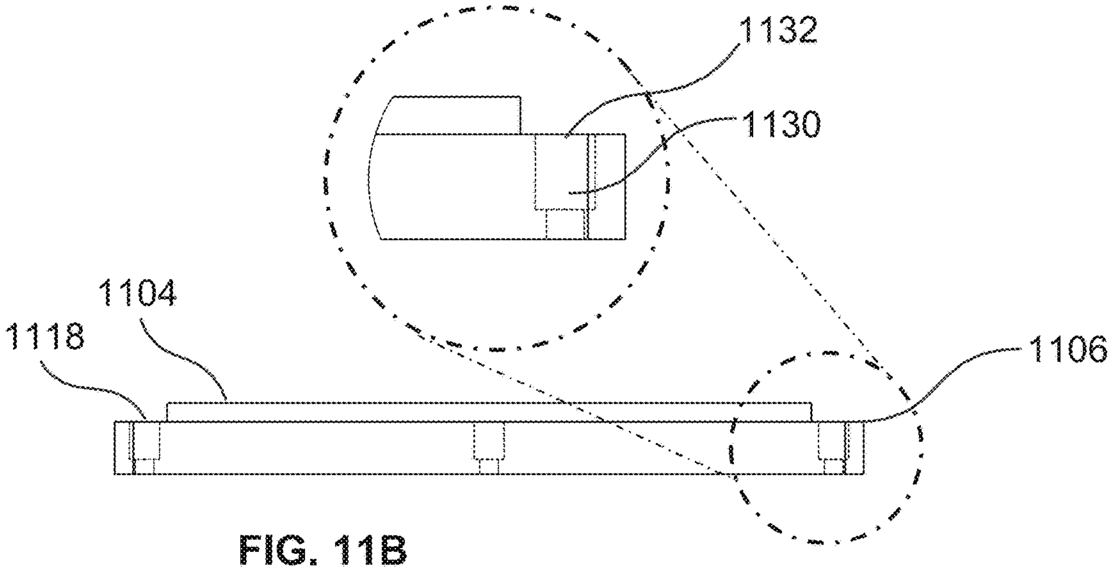

FIGS. 11A and 11B illustrate a base plate 1102 according to one embodiment of the disclosure in which the plurality of apertures 1118 or holes provided along the perimeter 1106 outside the elevated mounting face 1104 of the base plate 1102 comprise at least a first section 1130 having a diameter and a length and an opening 1132 flush with the surface of the perimeter 1106. FIG. 11A illustrates a top plan view of one embodiment of a base plate. FIG. 11B illustrates a plan side view of the base plate according to one embodiment showing the elevated mounting face 1104, and the plurality of apertures 1118 or holes position in the perimeter 1106 area of the side. The cut-out illustrates the structure of the plurality of apertures including at least a first section 1130 having a diameter and a length, and an opening flush with the surface of the perimeter 1106.

In some embodiments, the length and diameter of the base section of each of the plurality of elongate pins is less than the length and diameter of the first section of each of the plurality of apertures to thereby create a slip fit tolerance therebetween. Further, the top section of the plurality of elongate pins may be configured to be received within a separate respective aperture provided along the perimeter of the top plate, in some embodiments. The midsection of the plurality of elongate pins may be configured to be received within a separate respective aperture provided along the perimeter of the top plate. In this way, the plurality of elongate pins may be positioned within the respective apertures of the base plate and the top plate to secure, support, and compress the material layered between the base plate and the top plate.

In some embodiments, each of the plurality of apertures provided along the perimeter of the top plate may include at least a first section having a diameter and length such that the plurality of elongate pins align with and insert into the plurality of apertures of the top plate. In some embodiments, the length and diameter of the mid-section of each of the plurality of elongate pins is less than the length and diameter of the first section of each of the plurality of apertures provided along the perimeter of the top plate to thereby create a slip fit tolerance therebetween.

The plurality of elongate pins may be placed equidistantly apart along the perimeter of the base plate and the plurality of apertures may be correspondingly provided equidistantly apart along the perimeter of the top plate. In some embodiments, the base plate and the top plate may include additional apertures which may or may not be used, and/or may or may not be equidistantly spaced apertures. In some embodiments, the material layering tool may include apertures in the base plate such that the plurality of apertures include an adjustable slide for repositioning an elongate pin to accommodate flexible spacing of the elongate pins.

As disclosed herein, the material layering assembly may be used to support and/or hold various layers of material. For example, the material layering assembly may be used to support, secure, hold, and/or compress layers of tissue to form, for example, a multi-layered amnion (MLA) or multi-layer amnion/chorion product. Thus, in some embodiments, the one or more layers of material comprise at least tissue, for example, placental membrane, such that the material layering assembly is configured to hold multiple layers of placental membrane in a fixed position during a vacuum drying process.

Figure 12:
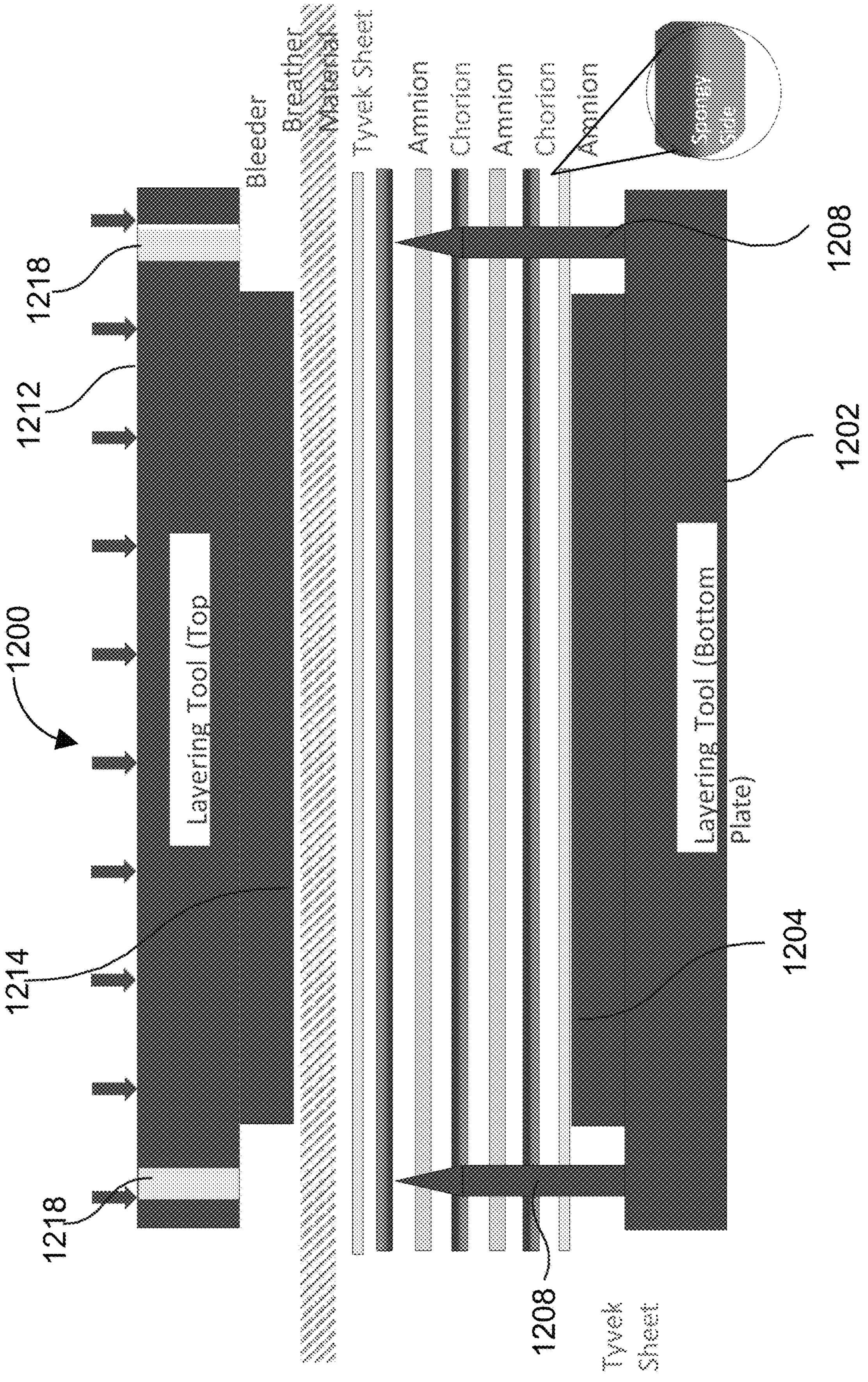
FIG. 12 illustrates one embodiment of a material layering assembly configured for use in the manufacture of a multi-layered amnion/chorion product.

FIG. 12 illustrates one embodiment of a material layering assembly 1200 configured for use in the manufacture of a dehydrated multi-layered placental amnion or amnion/chorion product. As illustrated, the material layering assembly is in a partially closed position with the top plate closing or being urged upon the layers of material retained by the plurality of pins on the base plate. Such a product may be a sheet that is configured to be placed around injured tissue, for example, injured nerves, including injured peripheral nerves. The multi-layer amnion or amnion/chorion product, e.g., sheet, may be used as a tissue covering to serve as an anatomical barrier to help provide protection from the surrounding environment.

As noted above, layering multiple placental membranes or other layers of tissue together is often difficult. The layering process often is performed when membranes or tissue layers are wet, which creates a variety of challenges. Placental membranes or tissue layers often retract or change shape in response to stretching, slide when placed on top of one another, and/or form air bubbles between layers. The material layering assemblies of the present invention allow for the manufacture of multi-layered placental membrane products that overcomes these obstacles. For example, the material layering assemblies retain each of the placental membrane or tissue layers in a stretched and/or flat orientation, and secures each layer in place, for example, to prevent sliding or other movement of the layers. Moreover, the material layering assemblies of the present invention provide for flattening the layers and/or compressing the layers together between the top plate and the base plate, thus helping to prevent or otherwise reduce air bubble formation and/or thus producing consistent product thickness throughout the resulting multi-layer amnion product.

Layers of tissue may be positioned on the base plate 1202, for example, spanning at least elevated face 1204. If pins 1208 are permanently received within apertures or holes of the base plate, or integrally formed with the base plate, then one or more chorion or amnion layers may be secured to elevated face 1204 of the base plate 1202 by pressing the layers down onto pins 1208 so that the layers extend over elevated face 1204. If pins 1208 are removably received within holes of the base plate and/or top plate, for example as described in FIG. 9, then layers of amnion or chorion may be positioned on base plate 1202, for example, spanning at least elevated face 1204.

In some embodiments, outer portions of each layer of tissue may be at least partially secured via respective holes in the base plate and/or pins 1208 by inserting pins 1208 through the layers and into the respective holes. For example, portions of each layer of tissue may be at least partially secured in respective holes via one or more pins, posts, pegs, sutures, wires, etc., passed through each layer of tissue and secured into a respective hole of the base plate and/or top plate.

In some embodiments, the tissue layers may include holes such that one or more ends of each of the plurality of pins may be tapered, sharpened, or otherwise shaped to form or be received within a respective opening in each layer of tissue.

In some embodiments, the plurality of pins may be fitted or otherwise positioned in respective holes, and the ends of pins, for example as shown in FIG. 12, may help to pierce respective portions of each layer of tissue. For example, the tapered, sharpened, or otherwise shaped ends of pins 1208 may help to pierce portions of each layer of tissue (e.g., as each layer of tissue is pushed down toward or otherwise positioned on base plate 1202), helping to retain the layers of tissue on the material layering assembly 1200.

In non-limiting examples, the types of tissue that may be used with the material layering assembly to manufacture a dehydrated tissue product include nerve tissue, such as peripheral nerve tissue or central nervous system tissue. Other types of tissue suitable for the present disclosure include, but are not limited to epithelial tissue, connective tissue, muscular tissue, tendon tissue, ligament tissue, vascular tissue, intestinal tissue, dermal tissue, and cardiac tissue. The tissue may be mammalian tissue, including human tissue and tissue of other primates, rodent tissue, equine tissue, canine tissue, rabbit tissue, porcine tissue, or ovine tissue. In addition, the tissue may be non-mammalian tissue, selected from piscine, amphibian, or insect tissue. The tissue may be allogeneic or xenogeneic to a subject into which the graft is implanted. The tissue may be a synthetic tissue, such as, but not limited to, laboratory-grown or 3D-printed tissue.

As illustrated in FIG. 12, the layers of may be alternating human placental sac amnion and chorion membranes. In some embodiments, the multiple layers comprise one or more layers of an amnion sheet and a chorion sheet. In some embodiments, debrided amnion membranes that have been cut into one or more of a 12×12 cm, 10×10 cm, or 8×8 cm size are layered on the material layering assembly. Likewise, debrided chorion membranes that have been cut into one of or more of a 12×12 cm, 10×10 cm, or 8×8 cm. Thus, the material layering assembly may be configured for a variety of shapes and/or sizes of debrided membranes.

The end product may be a dehydrated sheet composed of amnion layers or amnion/chorion layers. The product may be a multi-layer amnion (MLA) product, which may be a dehydrated sheet composed of, for example, at least 4 layers, for example, from 4 to 10 layers, from 4 to 7 layers, at least 4 layers and less than 10 layers of placental sac amnion or amnion and chorion membranes. The multi-layer amnion product may be a dehydrated sheet composed of at least 5 layers, for example, from 5 to 10 layers, from 5 to 7 layers, or from 5 to 6 layers of placental sac amnion or amnion and chorion membranes. The placental sac amnion and/or chorion membranes may be obtained from a human source, or, alternatively, a non-human source.

The amnion and chorion membrane layers may be component layers of the cross-section of human amniotic placental sac. An amnion membrane layer may include an epithelial layer, a basement membrane, and a fibroblast layer. A chorion membrane layer may include a reticular layer and, optionally, a basement membrane, but ideally omits most of, if not all, of the cells of a trophoblast layer. Additionally, a sponge layer may be positioned between the amnion membrane layer and the chorion membrane layer (e.g., between the fibroblast layer and the reticular layer). The fibroblast layer, the sponge layer, and the reticular layer are mesenchymal cells.

For example, as illustrated in FIG. 12, four or more layers of amnion and/or chorion may be sequentially positioned on the base layer 1202, one on top of the other, by piercing each layer of tissue with the plurality of pins 1208. In this way, the material layering tool holds the layers in place relative to each other when stacking them, provides tension to straighten out the layers, smooths the layers, sizes the layers, organizes the layers, promotes uniformity (e.g., facilitate the ability to position the layers so that they substantially overlap with one another in the same areas to promote consistent thickness of the resulting MLA product), removes air bubbles and/or prevents air bubbles from forming between the layers.

In some embodiments, the plurality of elongate pins 1208 are configured to pierce the one or more multiple layers of tissue such that each layer is stretched and held in place between the base plate 1202 and the top plate 1212 and maintained in a substantially flat orientation and wherein each sheet and the layers as a whole are prevented from sliding between the face of the base plate 1204 and the face of the top plate 1214. In this way, alignment and placement of the top plate 1212 upon the base plate 1202 causes the faces of the base and top plates to compress the multiple layers of tissue together and prevent air bubble formation and to form a multi-layered construct with a consistent thickness.

In a specific example, the material layering assembly may be used to stack multiple layers of placental membranes (chorion or amnion) together during a vacuum drying process. For example, in particular embodiments, the material layering assembly is designed to accommodate the 12×12 cm, 10×10 cm, or 8×8 cm sizes/segments of the amnion and/or chorion membranes. The base plate and top plate may be identical and interchangeable, each with eight apertures or holes in the perimeter section regardless of the size, such that the elongate pins are inserted into the apertures or holes of the base plate facing upward so that the pointed tip is vertical relative to the plate perimeter surface.

The assembly includes a bottom plate 1202 with 8 vertical pins 1218 or spikes, and top plate 1212 with 8 apertures 1218 or holes that are positioned to fit each pin 1208 or spike on bottom plate 1202. Each layer of the placental membrane may be placed on bottom plate 1202, such that a membrane layer is pierced with the plurality of pins 1208 or spikes. The pins or spikes may be used to stretch the placental membrane layers and keep them affixed as more layers are added to the multilayer amnion construct. Amnion and chorion segments may be stretched and pierced by the pins on the bottom plate one by one during the layering procedure. For example, a corner of the tissue layer may first be pierced by a pin positioned in a corner of the base plate, and then the remaining corners may be pierced, for example by working in a clockwise or counterclockwise manner. The remaining midpoint sections of the tissue segments may be pierced by the remaining four elongate pins positioned in the perimeter section of the base plate. The process may be repeated for each layer of tissue added to the base plate. The top plate may then be used to compress the layers of the amnion and chorion together once layers are in place by aligning the apertures of the top plate with the elongate pins positioned in the bottom plate.

After appropriate layers are stacked together, the top plate 1212 may be placed on top of bottom plate 1202, thus compressing or sandwiching the layers of placental membrane together. The entire construct retained on the material layering assembly may be then placed in vacuum bag and vacuum dried.

In some embodiments, a layer of non-placental material may be positioned between the layers of material stacked within the material layering assembly. For example, another biocompatible sheet of material, such as a polymer, e.g., one or more Tyvek sheets and/or breather material may be added to the layers of material. The Tyvek sheet may be positioned between the top plate and the final amnion layer. In some embodiments, portions of the another Tyvek sheet may be secured via one or more pins or other securing mechanisms in the apertures or holes. In some embodiments, at least four or at least five layers of amnion or amnion and chorion may be overlaid within the material layering assembly, for example, with epithelial cells of the outermost amnion layers facing outward on both sides of the overlaid layers. In other embodiments, each layer may be positioned on a biocompatible sheet of material, and the layer and the biocompatible sheet of material may be positioned on the base plate. In some embodiments, the biocompatible sheet of material may be removed after each layer is positioned on the base plate, for example, once the respective layer is secured via one or more of the plurality of pins.

Accordingly, material layering assemblies of the present disclosure provide for improved multi-layered tissue products as measured by qualities and handling properties such as, for example, appearance, conformability, repositionability, durability, suturability, and level of delamination of layers. The multi-layer amnion product may have superior handling properties around tissues, e.g., peripheral nerves, compared with other dehydrated amniotic sac based membranes. Exemplary superior handling properties may include one or more of the following: conformability around tissue such as a nerve, the ability to hold a suture, the ability to be moved freely as a sheet in both a dehydrated or rehydrated state, the ability to be repositioned after being placed on one or more tissues, etc. Such handling properties may not be as important when used for external purposes, e.g., on wounds, but may be of particular interest when wrapping around or conforming to internal tissues like nerves. For example, improved properties may allow a surgeon to position, wrap, reposition, secure, visualize, etc., the multi-layer amnion product when positioning the product relative to a tissue within the body. The improved products may be suitable for use with tissues within the body rather than only wound care. The improved products may have resorption kinetics suitable for use with internal tissues within the body, e.g., for use with nerves, such that the product may resorb after approximately four weeks, after approximately five weeks, after approximately six weeks, or after approximately seven weeks, e.g., in approximately four to eight weeks, or approximately six to eight weeks. While products used for application on wounds may be reapplied at regular intervals, products applied internally, e.g., to nerves, cannot be reapplied without surgical intervention. Accordingly, the material layering assemblies of the present disclosure provide for improved multi-layer tissue products that may have resorption times that allow the product to stay in place long enough for the tissue to heal.

Figure 13:
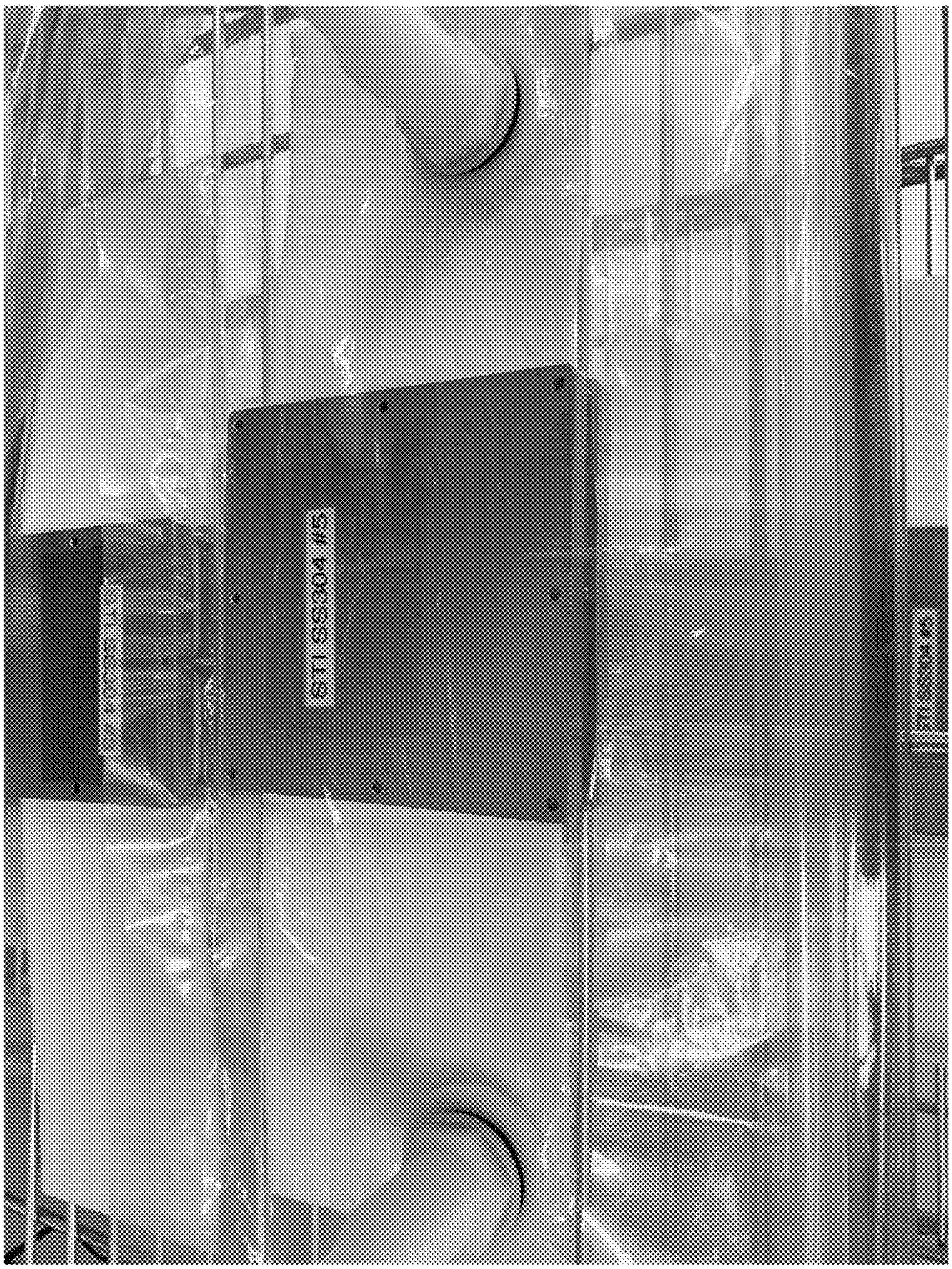
FIG. 13 illustrates one embodiment of a material layering assembly according to the disclosure in a closed configuration and containing a layered tissue product therein, and contained within a vacuum bag for further dehydration.

FIG. 13 illustrates one embodiment of a material layering assembly 1300 according to the disclosure in a closed configuration and containing a layered tissue product therein, and contained within a vacuum bag for further dehydration.

Figure 14:
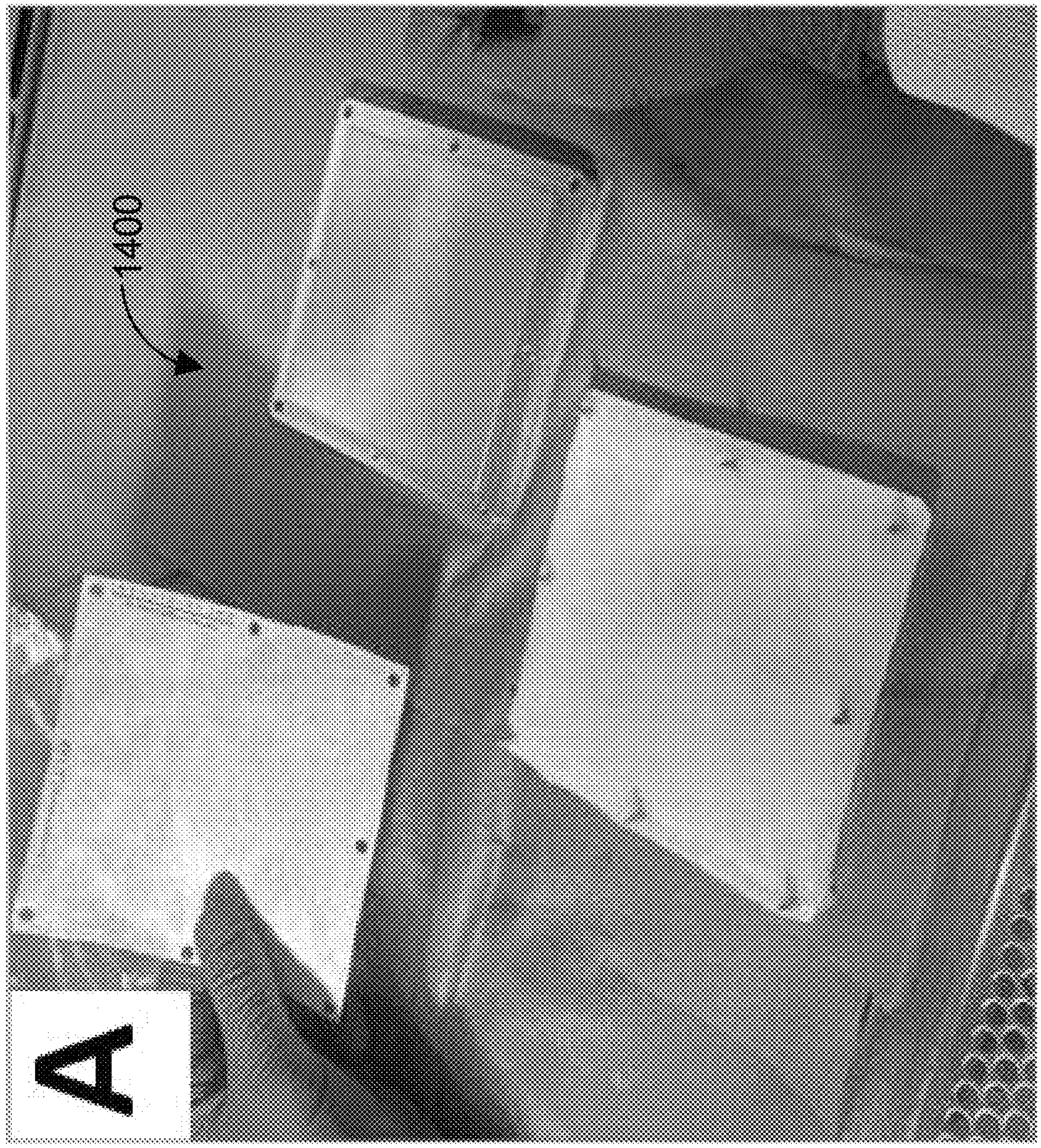
FIG. 14 illustrates one embodiment of a material layering assembly according to the disclosure in an open configuration in which an amnion/chorion tissue product has been dehydrated and is ready for removal from the assembly.

FIG. 14 illustrates one embodiment of a material layering assembly 1400 according to the disclosure in an open configuration in which an amnion/chorion tissue product has been dehydrated and is ready for removal from the assembly.

In some embodiments, the material layering assembly includes a tool for placing the tissue layers on the base plate. The tool may be, for example, shaped to position the tissue over the base plate and press the tissue onto the elongate pins to contact the elevated face of the base plate. In some embodiments, a force is applied to the tool to gently pierce the tissue and position the layer within the material layering assembly.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

The invention claimed is:

1. A material layering assembly comprising:

a base plate comprising a face having a planar surface and a perimeter surrounding the face, wherein the perimeter comprises a plurality of pins extending out from the perimeter of the base plate; and a top plate comprising a face having a planar surface and a perimeter surrounding the face, wherein the perimeter of the top plate comprises a plurality of apertures, wherein, when the face of the base plate and the face of the top plate are aligned with one another, the plurality of apertures of the top plate are sized and shaped to receive a respective one of the plurality of pins extending from the surface of the perimeter of the base plate to thereby align the faces of the base and top plates relative to one another and cause one or more layers of material placed upon the base plate to be held between the faces of the base and top plates.

2. The assembly of claim 1, wherein the faces of the base and top plates are elevated relative to the respective perimeters of the base and top plates.

3. The assembly of claim 1, wherein the perimeter of each of the base and top plates comprises a reduced-thickness edge such that the face is raised in relation to the perimeter.

4. The assembly of claim 3, wherein, when the top plate is aligned relative to the base plate, the faces of the base and top plates are aligned with one another such that one or more layers of tissue therebetween are compressed between the faces of the base and top plates and the plurality of pins extending from the perimeter of the base plate and received within corresponding apertures of the perimeter of the top plate are not load-bearing.

5. The assembly of claim 1, wherein each of the base and top plates is of unitary construction.

6. The assembly of claim 5, wherein each of the base and top plates is formed from a single piece of material via an additive manufacturing process or a subtractive manufacturing process.

7. The assembly of claim 1, wherein each of the plurality of pins is removably attachable to the perimeter of the base plate.

8. The assembly of claim 7, wherein each of the plurality of pins comprises a base section configured to engage with the perimeter of the base plate.

9. The assembly of claim 8, wherein the base section of each of the plurality of pins is configured to releasably fit within a respective aperture located in the perimeter of the base plate.

10. The assembly of claim 9, wherein the base section of each of the plurality of pins is configured to releasably fit within a respective aperture via a slip fit connection.

11. The assembly of claim 10, wherein each of the plurality of apertures located in the perimeter of the base plate comprises at least a first section having a diameter and length and an opening flush with a surface of the perimeter.

12. The assembly of claim 11, wherein a length and a diameter of the base section of each of the plurality of pins is less than the length and diameter of the first section of each of the plurality of apertures to thereby create a slip fit tolerance therebetween.

13. The assembly of claim 1, wherein each of the plurality of pins comprises a top section configured to be received within a respective aperture along the perimeter of the top plate.

14. The assembly of claim 13, wherein the top section of each of the plurality of pins is cylindrically tapered and comprises a tip for piercing one or more layers of material.

15. The assembly of claim 14, wherein the top section reduces in diameter over 7.50 mm from 2.50 mm to 0.80 mm at the tip.

16. The assembly of claim 14, wherein the top section reduces in diameter over 7.50 mm from 3.00 mm to 0.80 mm at the tip.

17. The assembly of claim 14, wherein the top section reduces in diameter over 8.00 mm from 3.00 mm to 1.00 mm at the tip.

18. The assembly of claim 1, wherein each of the plurality of pins comprises a mid-section configured to be received within a respective aperture along the perimeter of the top plate.

19. The assembly of claim 18, wherein each of the plurality of apertures along the perimeter of the top plate comprises at least a first section having a diameter and length.

20. The assembly of claim 19, wherein a length and a diameter of the mid-section of each of the plurality of pins is less than the length and diameter of the first section of each of the plurality of apertures provided along the perimeter of the top plate to thereby create a slip fit tolerance therebetween.

21. The assembly of claim 1, wherein the plurality of pins are spaced equidistantly apart along the perimeter of the base plate, and the plurality of apertures are correspondingly spaced equidistantly apart along the perimeter of the top plate.

22. The assembly of claim 1, wherein the base plate, the top plate, and the plurality of pins comprise a material that is capable of cleaning, autoclaving, and reuse without warping.

23. The assembly of claim 22, wherein the material comprises stainless steel.

24. The assembly of claim 1, wherein the one or more layers of material comprises at least tissue.

25. The assembly of claim 24, wherein the tissue is placental membrane and wherein the assembly is configured to hold multiple layers of placental membrane in a fixed position during a vacuum drying process.

26. The assembly of claim 25, wherein the multiple layers comprise one or more layers of an amnion sheet and a chorion sheet.

27. The assembly of claim 26, wherein the plurality of pins are configured to pierce the one or more multiple layers of tissue such that each layer is stretched and held in place between the base and top plates and maintained in a substantially flat orientation and inhibited from sliding between the faces of the base and top plates.

28. The assembly of claim 27, wherein alignment of the top plate and the base plate causes the faces of the base and top plates to compress the multiple layers of tissue together and inhibit air bubble formation and to form a multi-layered construct with a consistent thickness.

* * * * *